ID

US009315782B2

(12) United States Patent
Yoshida et al.

(10) Patent No.: US 9,315,782 B2
(45) Date of Patent: Apr. 19, 2016

(54) ISOLATED DNA ENCODING PROTEIN HAVING IMPROVED STABILITY

(75) Inventors: Shinichi Yoshida, Takasago (JP); Akira Iwasaki, Takasago (JP); Motohisa Washida, Takasago (JP); Tozo Nishiyama, Takasago (JP); Daisuke Moriyama, Takasago (JP); Naoaki Taoka, Takasago (JP)

(73) Assignee: Kaneka Corporation, Osaka-shi (JP)

( * ) Notice: Subject to any disclaimer, the term of this patent is extended or adjusted under 35 U.S.C. 154(b) by 392 days.

(21) Appl. No.: 13/574,458

(22) PCT Filed: Jan. 19, 2011

(86) PCT No.: PCT/JP2011/050824
§ 371 (c)(1),
(2), (4) Date: Oct. 12, 2012

(87) PCT Pub. No.: WO2011/090054
PCT Pub. Date: Jul. 28, 2011

(65) Prior Publication Data
US 2013/0030164 A1 Jan. 31, 2013

(30) Foreign Application Priority Data
Jan. 20, 2010 (JP) ................................. 2010-010308

(51) Int. Cl.
C07H 21/00 (2006.01)
C12N 15/00 (2006.01)
C12N 15/53 (2006.01)
C12N 1/21 (2006.01)
C12N 5/10 (2006.01)
C12N 1/15 (2006.01)
C12N 9/08 (2006.01)
C12N 9/02 (2006.01)
C12P 19/36 (2006.01)
C12P 7/02 (2006.01)
C12P 7/18 (2006.01)
C12P 7/42 (2006.01)
C12P 13/04 (2006.01)

(52) U.S. Cl.
CPC ............ *C12N 9/0065* (2013.01); *C12N 9/0036* (2013.01); *C12P 7/02* (2013.01); *C12P 7/18* (2013.01); *C12P 7/42* (2013.01); *C12P 13/04* (2013.01); *C12P 19/36* (2013.01); *C12Y 106/03001* (2013.01); *C12Y 111/01001* (2013.01)

(58) Field of Classification Search
CPC .. C12N 9/0036; C12N 9/0065; C12N 9/0006; C12N 9/0008; C12N 9/0012; C12N 9/0016; C12P 7/18; C12P 13/04; C12P 7/02; C12P 19/36; C12P 7/42; C12Y 106/03001; C12Y 111/01001; C12Y 101/01304; Y02E 50/10

USPC ............ 435/189, 320.1, 69.1, 325, 252.3, 25; 536/23.2
See application file for complete search history.

(56) References Cited

U.S. PATENT DOCUMENTS

| 5,334,507 A | 8/1994 | Soya et al. |
| 5,763,236 A | 6/1998 | Kojima et al. |
| 8,129,163 B2 | 3/2012 | Kawano et al. |
| 2003/0100065 A1 | 5/2003 | Hummel et al. |
| 2004/0248250 A1 | 12/2004 | Nakai et al. |
| 2007/0292923 A1* | 12/2007 | Iwasaki et al. .................. 435/90 |
| 2008/0038803 A1 | 2/2008 | Iwasaki et al. |
| 2010/0035317 A1 | 2/2010 | Kawano et al. |
| 2013/0030164 A1 | 1/2013 | Yoshida et al. |

FOREIGN PATENT DOCUMENTS

| CN | 101407780 B | 8/2010 |
| EP | 0 533 183 A2 | 3/1993 |
| EP | 0 645 453 A2 | 3/1995 |
| EP | 1 241 598 A1 | 9/2002 |
| EP | 2 096 165 A1 | 9/2009 |
| JP | 5103697 A | 4/1993 |
| JP | 7231785 A | 9/1995 |
| JP | 08-196281 A | 8/1996 |
| JP | 2003-116585 A | 4/2003 |
| JP | 2003-169696 A | 6/2003 |
| JP | 3574682 | 10/2004 |
| JP | 2005-102511 A | 4/2005 |
| JP | 2005533497 | 11/2005 |
| WO | WO-03/004653 A1 | 1/2003 |
| WO | WO-2004/009807 A1 | 1/2004 |
| WO | WO-2006/013802 A1 | 2/2006 |
| WO | WO-2006/033333 A1 | 3/2006 |
| WO | WO-2006/090814 A1 | 8/2006 |
| WO | WO-2008/066018 A1 | 6/2008 |

OTHER PUBLICATIONS

Branden et al., Introduction to Protein Structure, Garland Publishing Inc., New York, p. 247, 1991.*

(Continued)

*Primary Examiner* — Delia Ramirez
(74) *Attorney, Agent, or Firm* — Novak Druce Connolly Bove + Quigg LLP

(57) ABSTRACT

Water-forming NADH oxidase derived from *Streptococcus mutans* should be further improved in terms of stability for practical use in industrial production. An object of the present invention is to provide an enzyme that is obtained through modification of a water-forming NADH oxidase, which is useful as an NAD+ regeneration system for stereoselective oxidation catalyzed by an oxidoreductase, by protein engineering techniques so that the enzyme can withstand long-term use without exhibiting a reduction of its activity for the regeneration of NAD+, that is, an enzyme having improved stability, and to provide a method for efficiently producing a useful substance such as an optically active alcohol or amino acid. The present invention relates to an enzyme modification method that can improve the stability of water-forming NADH oxidase derived from *Streptococcus mutans* by appropriately introducing mutation.

8 Claims, No Drawings

(56) References Cited

OTHER PUBLICATIONS

Seffernick et al., J. Bacteriol. 183(8):2405-2410, 2001.*
Witkowski et al., Biochemistry 38:11643-11650, 1999.*
Guo et al., PNAS 101(25):9205-9210, 2004.*
Genbank accession No. WP_003080172, May 2013.*
GenBank accession No. WP_018364669, Jun. 2013.*
Richards et al. GenBank accession No. AEUW02000001, Nov. 18, 2011.*
Richards et al. GenBank accession No. EHJ52306, Nov. 18, 2011.*
Nippon Nogei Kagakukai Taikai Koen Yoshishu, 2009, p. 121, 2P0968B.
Matsumoto et al., "Molecular Cloning and Sequence Analysis of the Gene Encoding the $H_2O$-forming NADH Oxidase from *Streptococcus mutans*", Biosci. Biotechnol. Biochem., 1996, 60 (1), pp. 39-43.
Liese et al., "Industrial Biotransformations," John Wiley & Sons, Jun. 12, 2008, pp. 40-42.
Wandrey et al., "Industrial Biocatalysis: Past, Present, and Future", Organic Process Research & Development, 2000, vol. 4, pp. 286-290.
Chenault et al., "Regeneration of Nicorinamide Cofactors for Use in Organic Synthesis", Applied BioChemistry and Biotechnology, 1987, vol. 14, pp. 147-197.
Kroutil et al., "Recent Advances in the Biocatalytic Reduction of Ketone and Oxidation of sec-alcohols", Current Opinion in Chemical Biology, 2004, vol. 8, pp. 120-126.
Geueke et al., "NADH Oxidase from *Lactobacillus brevis*: A New Catalyst for the Regeneration of NAD", Enzyme and Microbial Technology, 2003, vol. 32, pp. 205-211.
Riebel et al., Cofactor Regeneration of Both NAD+ from NADH and NADP+ from NADPH:NADH Oxidase from *Lactobacillus sanfranciscensis*, Adv. Synth. & Catal., 2003, vol. 345, pp. 707-712.
Hummel et al., "An Efficient and Selective Enzymatic Oxidation System for the Synthesis of Enantiomerically Pure D-tert-Leucine", Orangic Letters, 2003, vol. 5, No. 20, pp. 3649-3650.
Findrik et al., "Coenzyme Regeneration Catalyzed by NADH Oxidase from *Lactobacillus brevis* in the Reaction of L-Amino Acid Oxidation", Biochemical Engineering Journal, 2008, vol. 39, pp. 319-327.
Higuchi et al., "Identification of Two Distinct NADH Oxidases Corresponding to $H_2O_2$-Forming Oxidase and $H_2O$-forming Oxidase Induced in *Stretococcus mutans*", Journal of General Microbiology, 1993, vol. 139, pp. 2343-2351.
Matsumoto et al., "Molecular Cloning and Sequence Analysis fo the Gene Encoding the $H_2O$-forming NADH Oxidase from *Streptococcus mutans*", Biosci. Biotechnol. Biochem., 1996, vol. 60, No. 1, pp. 39-43.
Higuchi et al., "Functions of Two Types of NADH Oxidases in Energy Metabolism and Oxidative Stress of *Streptococcus mutans*", Journal of Bacteriol., 1999, vol. 181, No. 19, pp. 5940-5947.
English translation of International Preliminary Report on Patentability (Chapter I) issued in International Appln No. PCT/JP2011/050824 dated Aug. 7, 2012.
Auzat et al., "The NADH Oxidase of *Streptococcus pneumoniae*: Its Involvement in Competence and Virulence", Molecular Microbiology (1999) 34(5), 1018-1028.
Akada et al., "Construction of Recombinant Sake Yeast Containing a Dominant FAS2 Mutation without Extraneous Sequences by a Two-Step Gene Replacement Protocol", Journal of Bioscience and Bioengineering, vol. 87, No. 1, 43-48, 1999.
International Preliminary Report on Patentability and Written Opinion of the International Searching Authority (Forms PCT/IB/373 and PCT/ISA/237) and English translation thereof, dated Aug. 7, 2012, for International Application No. PCT/JP2011/050824.
International Preliminary Report on Patentability and Enclish translation of the Written Opinion of the International Searching Authority (Forms PCT/IB/373 and PCT/ISA/237) dated Jun. 3, 2009 for International Application No. PCT/JP2007/072803.
U.S. Notice of Allowance dated Aug. 31, 2011 for U.S. Appl. No. 12/516,388.
U.S. Office Action dated Apr. 12, 2011 for U.S. Appl. No. 12/516,388.
Larroy et al., "Characterization of a *Saccharomyces cerevisiae* NADP(H)-dependent alcohol dehydrogenase (ADHVII), a member of the cinnamyl alcohol dehydrogenase family", Eur, J. Biochem. 269, 5738-5745, 2002.
English translation of International Preliminary Report on Patentability and Written Opinion mailed Jan. 16, 2014 in PCT International Application No. PCT/JP2012/066418.
Khoury et al., "Computation design of Candida boldini xylose reductase for altered cofactor specificity", Protein Science (2009) vol. 19, pp. 2125-2138.
Machielsen et al., "Cofactor engineering of Lactobacillus brevis alcohol dehydrogenase by computational design", Eng. Life Sci. (2009) vol. 9, No. 1, pp. 38-44.
McKeever et al., "Amino acid substitution of arginine 80 in 17β-hydroxysteroid dehydrogenase type 3 and its effect on NADPH cofactor binding and oxidation/reduction kinetics", Biochimica et Biophysica Acta (2002) vol. 1601, pp. 29-37.
Nakanishi et al., "Switch of Coenzyme Specifically of Mouse Lung Carbonyl Reductase by Substitution of Threonine 38 with Aspartic Acid" J. Biol. Chem. (Jan. 24, 1997) vol. 272, No. 4, pp. 2218-2222.
Penning et al., "Enzyme Redesign", Chem. Rev. (2001) vol. 101, pp. 3027-2046.
Tanaka et al., "Crystal structure of the ternary complex of mouse lunch carbonyl reductase at 1.8 Å resolution: the structural original of coenzyme specificity in the short-chaim dehydrogenase/reductase family", Structure (Jan. 15, 1996) vol. 4, pp. 33-45.
Zhang et al., "Ser67Asp and His68Asp Substitutions in Candida parapsilosis Carbonyl Reductase Alter the Coenzyme Specificity and Enantioselectivity of Ketome Reduction", Applied and Environmental Microbilogy (Apr. 2009) vol. 75, No. 7, pp. 2176-2183.
Serov et al., "Engineering of coenzyme specificity of formate dehydrogenase from *Saccharomyces cerevisiae* ", Biochem. J. (2002) vol. 367, pp. 841-847.
Ehsani et al., "Reversal of Coenzyme Specificity of 2,3-Butanediol Dehydrogenase from *Saccharomyces cerevisae* and In Vivo Functinal Analysis", Biotechnology and Bioengineering, Oct. 1, 2009, vol. 104, No. 2, pp. 381-389.
Gibrat et al., "Surprising similarities in structure comparison", Current Opinion in Structural Biology, 1996, vol. 6, No. 3, pp. 377-385.
Nordiing et al., "Medium-chaim dehydrogenases/reductases (MDR)", Eur. J. Biochem., 2002, vol. 269, No. 17, pp. 4267-4276.
Watanabe et al., "Complete Reversal of Coenzyme Specificity of Xulitol Dehydrogenase and Increase of Termostability by the Introduction of Structural Zinc", J. of Biological Chemistry, 2005, vol. 280, No. 11, pp. 10340-10349.
Chica et al., "Semi-rational approaches to engineering enzyme activity: combining the benefits of directed evolution and rational design", Current Opinion in Biotechnology, vol. 16, 2005 (Published online Jul. 1, 2005), pp. 378-384.
Sen et al., "Developments in Directed Evolution for Improving Enzyme Functions", Appl. Biochem. Biotechnol., vol. 143, 2007, pp. 212-223.
Acession AB10636. Published Jan. 28, 1998.
UNIPROT: Q5A958 (XP002561805). Apr. 26, 2005.
GENESEQP: AAY95047 (XP002561806). Jun. 23, 2000.
JPOP: BD675875 (XP002561807). Nov. 19, 2003.
Accession O42703. Published Jun. 1, 1998.
Current Protocols in Molecular Biology, Preparations and Analysis of DNA, Supplement 21 pp. 2.10.8-2.10-11, Jan. 1993.
Accession No. F2L599, version 1, UniProt [online].
Accession No. P42327, version 65, UniProt [online].

* cited by examiner

ISOLATED DNA ENCODING PROTEIN HAVING IMPROVED STABILITY

CROSS REFERENCE TO RELATED APPLICATIONS

This application is a National Phase filing under 35 U.S.C. §371 of PCT/JP2011/050824 filed on Jan. 19, 2011; and this application claims priority to Application No. 2010-010308 filed in Japan on Jan. 20, 2010 under 35 U.S.C. §119; the entire contents of all are hereby incorporated by reference.

TECHNICAL FIELD

The present invention relates to NAD(P)H oxidase variants.

BACKGROUND ART

Reactions that involve oxidoreductases activated by the coenzyme nicotinamide adenine dinucleotide to synthesize compounds of interest are widely used in industrial processes. Many of these compounds of interest are optically active compounds which are mainly produced as precursors of medicaments and agricultural chemicals (Non Patent Literatures 1 and 2). The redox reactions involving oxidoreductases are accompanied with either the conversion of NAD(P)+ (oxidized coenzyme) into NAD(P)H (reduced coenzyme) or the reverse conversion of NAD(P)H into NAD(P)+. Therefore, these redox reactions require a stoichiometric amount of NAD(P)+ or NAD(P)H. In industrial processes, it is preferable to avoid the use of a stoichiometric amount of such an expensive coenzyme. In this context, a technique that can reduce the amount of the expensive coenzyme has been used in industrial fields, in which the redox reaction is coupled with the conversion of the coenzyme formed as a result of the redox reaction into the form reusable for the reaction (oxidized form or reduced form) (Non Patent Literatures 2 and 3).

NAD(P)H oxidases are one of oxidoreductases that can be used for the conversion of NAD(P)H into NAD(P)+. Oxidation reactions of alcohols, amino acids, and the like which are catalyzed by nicotinamide coenzyme-dependent oxidoreductases utilize NAD(P)+ and produce NAD(P)H. NAD(P)H oxidases, which catalyze the conversion of NAD(P)H into NAD(P)+, can be involved in the oxidation of alcohols, amino acids, and the like, as an enzyme for regenerating NAD(P)+ (as a second enzyme system) (Patent Literatures 1 to 3 and Non Patent Literatures 3 and 4).

Well-known NAD(P)H oxidases used for industrial purposes are ones that produce a by-product such as hydrogen peroxide ($H_2O_2$) or water ($H_2O$) as a result of reduction of molecular oxygen which occurs simultaneously with the oxidation of NAD(P)H to NAD(P)+ (Non Patent Literatures 3 and 4). Water-forming NAD(P)H oxidases are suitable for the NAD(P)+ regeneration system since they irreversibly catalyze the production of NAD(P)+ from NAD(P)H. $H_2O_2$-forming NAD(P)H oxidases are not easily used for enzyme-involved chemical reaction processes because produced $H_2O_2$ is toxic to enzymes. Therefore, ones that produce only water as a reaction product in addition to NAD(P)+ are preferred for industrial purposes.

Examples of known water-forming NAD(P)H oxidases include NADH oxidase derived from *Lactobacillus brevis*, NADH/NADPH (both can be substrates) oxidase derived from *Lactobacillus sanfranciscensis*, NADH oxidase derived from *Pyrococcus furiosus*, and NADH oxidase derived from *Borrelia burgdorferi* (Non Patent Literatures 4 to 6). Methods for synthesizing an optically active compound (optical resolution) have been proposed which utilize such a water-forming NAD(P)H oxidase as an NAD(P)+ regeneration system (Patent Literature 1 and Non Patent Literatures 5 to 8).

Water-forming NADH oxidases derived from bacteria of *Streptococcus*, in particular *Streptococcus mutans*, are also known (Patent Literature 2 and Non Patent Literatures 9 to 11). It has already been verified that these enzymes can be used as second enzyme systems for regenerating NAD(P)+ in oxidation reactions of alcohols, amino acids, and the like which are catalyzed by nicotinamide coenzyme-dependent oxidoreductases (Patent Literatures 3 and 4). These enzymes are characteristically known to efficiently catalyze the regeneration of NAD+ in the absence of enzyme stabilizers such as reductants (Patent Literature 2). This is a superior characteristic in terms of industrial usability, compared with other NAD(P)H oxidases such as NADH oxidase derived from *Lactobacillus brevis* which require an additive such as DTT (dithiothreitol) (Non Patent Literature 5).

CITATION LIST

Patent Literature

Patent Literature 1: JP-A 2003-116585
Patent Literature 2: JP-A H08-196281
Patent Literature 3: WO 06/013802
Patent Literature 4: WO 06/033333

Non Patent Literature

Non Patent Literature 1: Liese A. et al. "Industrial Biotransformations", Wiley-VCH
Non Patent Literature 2: Wandrey C. et al., "Organic Process Research & Development", 2000, Vol. 4, 286-290
Non Patent Literature 3: Chenault H. K. et al., "Applied BioChemistry and Biotechnology", 1987, vol. 14, 147-197
Non Patent Literature 4: Kroutil W. et al., "Current Opinion in Chemical Biology", 2004, Vol. 8, 120-126
Non Patent Literature 5: Geueke B. et al., "Enzyme and MicroBial Technology", 2003, Vol. 32, 205-211
Non Patent Literature 6: Riebel B. R. et al., "Advanced Synthesis & Catalysis", 2003, Vol. 345, 707-712
Non Patent Literature 7: Hummel W. et al., "Organic Letters, 2003, Vol. 5, 3649-3650
Non Patent Literature 8: Findrik Z. et al., "Biochemical Engineering Journal", 2008, Vol. 39, 319-327
Non Patent Literature 9: Higuchi M. et al., "Journal of General Microbiology", 1993, Vol. 139, 2343-2351
Non Patent Literature 10: Matsumoto J. et al., "Bioscience, Biotechnology, and Biochemistry", 1996, Vol. 601, 39-43
Non Patent Literature 11: Higuchi M. et al., "Journal of Biotechnology", 1999, Vol. 181, 5940-5947

SUMMARY OF INVENTION

Technical Problem

Water-forming NADH oxidase derived from, Streptococcus mutans should be further improved in terms of safety for practical use in industrial production. Specifically, it has been found to have a disadvantage in that the enzyme activity for the regeneration of NAD+ remarkably reduces with time. An object of the present invention is to provide an enzyme that is obtained through modification of a water-forming NADH oxidase, which is useful as an NAD+ regeneration system for stereoselective oxidation catalyzed by an oxidoreductase, by protein engineering techniques so that the enzyme can withstand long-term use without exhibiting a reduction of its activity for the regeneration of NAD+, that is, an enzyme having improved stability, and to provide a method for efficiently producing a useful substance such as an optically active alcohol or amino acid.

Solution to Problem

As a result of intensive studies to overcome the above problem, the present inventors have developed a novel enzyme modification method that can improve the stability of water-forming NAD(P)H oxidase derived from *Streptococcus mutans*. This method can therefore be employed as an enzyme modification method for improving the stability of NAD(P)H oxidases which have high sequence identity thereto.

Specifically, the present invention relates to the following.

[1] A protein having an amino acid sequence that has at least 85% sequence identity to the amino acid sequence of SEQ ID No:1, and further contains at least one amino acid substitution selected from (o) to (u):

(o) a substitution of an amino acid residue at a position conformationally equivalent to Leu-'42 with an amino acid having a side-chain surface area of 100 to 200 ($Å^2$);

(p) a substitution of an amino acid residue at a position conformationally equivalent to Met-46 with a neutral amino acid having a side-chain surface area of 100 to 150 ($Å^2$) or an acidic amino acid having a side-chain surface area of 100 to 150 ($Å^2$);

(q) a substitution of an amino acid residue at a position conformationally equivalent to Asn-96 with a basic amino acid;

(r) a substitution of an amino acid residue at a position conformationally equivalent to Tyr-172 with an amino acid having a smaller side-chain surface area than Tyr;

(s) a substitution of an amino acid residue at a position conformationally equivalent to Thr-196 with a basic amino acid;

(t) a substitution of an amino acid residue at a position conformationally equivalent to Ala-312 with an amino acid having a larger side-chain surface area than Ala; and (u) a substitution of an amino acid residue at a position conformationally equivalent to Phe-371 with an aliphatic amino acid, an acidic amino acid, or an amino acid having a hydroxyl group-bearing side chain.

[2] The protein defined in [1],
wherein the amino acid sequence contains at least one amino acid substitution selected from (v) to (bb):

(v) a substitution of an amino acid residue at a position conformationally equivalent to Leu-42 with Met;

(w) a substitution of an amino acid residue at a position conformationally equivalent to Met-46 with Ile;

(x) a substitution of an amino acid residue at a position conformationally equivalent to Asn-96 with Arg or His;

(y) a substitution of an amino acid residue at a position conformationally equivalent to Tyr-172 with Ala or Ser;

(z) a substitution of an amino acid residue at a position conformationally equivalent to Thr-196 with His;

(aa) a substitution of an amino acid residue at a position conformationally equivalent to Ala-312 with Ile; and (bb) a substitution of an amino acid residue at a position conformationally equivalent to Phe-371 with Ala, Val, Ile, Glu, Ser, Thr, or Tyr.

[3] A protein including an amino acid sequence of SEQ ID No:1 which further contains at least one amino acid substitution selected from (a) to (g):

(a) a substitution of Leu-42 with an amino acid having a side-chain surface area of 100 to 200 ($Å^2$);

(b) a substitution of Met-46 with a neutral amino acid having a side-chain surface area of not more than 150 ($Å^2$) or an acidic amino acid having a side-chain surface area of not more than 150 ($Å^2$);

(c) a substitution of Asn-96 with a basic amino acid;

(d) a substitution of Tyr-172 with an amino acid having a smaller side-chain surface area than Tyr;

(e) a substitution of Thr-196 with a basic amino acid;

(f) a substitution of Ala-312 with an amino acid having a larger side-chain surface area than Ala; and (g) a substitution of Phe-371 with an aliphatic amino acid, an acidic amino acid, or an amino acid having a hydroxyl group-bearing side chain.

[4] The protein defined in [3],
wherein the amino acid sequence contains at least one amino acid substitution selected from (h) to (n):

(h) a substitution of Leu-42 with Met;
(i) a substitution of Met-46 with Ile;
(j) a substitution of Asn-96 with Arg or His;
(k) a substitution of Tyr-172 with Ala or Ser;
(l) a substitution of Thr-196 with His;
(m) a substitution of Ala-312 with Ile; and
(n) a substitution of Phe-371 with Ala, Val, Ile, Glu, Ser, Thr, or Tyr.

[5] The protein defined in claim 4,
wherein the protein has an amino acid sequence selected from the amino acid sequences of SEQ ID Nos:2 and 4 to 19.

[6] A DNA encoding a protein defined in any one of [1] to [5].

[7] A vector containing the DNA defined in [6].

[8] A transformant obtained by transformation with the vector defined in [7].

[9] A culture of the transformant defined in [8].

[10] An enzyme variant-containing product obtained by processing the culture defined in [9].

[11] A method for converting NADH/NADPH (a reduced form) to NAD+/NADP+ (an oxidized form) using the protein defined in any one of [1] to [5].

[12] The method defined in [11],
wherein the NADH/NADPH (the reduced form) is produced in a reaction catalyzed by an oxidoreductase with nicotinamide adenine dinucleotide as a coenzyme.

[13] The method defined in [11] or [12],
wherein the method utilizes the transformant defined in [8], the culture of the transformant defined in [9], or the enzyme variant-containing product defined in [10].

[14] A compound produced by the method defined in any one of [11] to [13].

[15] The method defined in [12] or [13],
wherein the reaction catalyzed by an oxidoreductase with nicotinamide adenine dinucleotide as a coenzyme is selective oxidation of one enantiomer.

[16] An optically active compound having a high enantiomeric excess, produced by the method defined in [15].

Advantageous Effects of Invention

The NADH oxidases or NADPH oxidases having improved stability according to the present invention can withstand long-term use without exhibiting a reduction of its activity for the regeneration of NAD+ or NADP+, and therefore efficiently allows the regeneration to proceed. If this coenzyme regeneration system is coupled with stereoselective oxidation catalyzed by an oxidoreductase, an optically active compound having a high enantiomeric excess can then be efficiently obtained from an enantiomer mixture.

DESCRIPTION OF EMBODIMENTS

The polypeptide of SEQ ID No:1 is water-forming NADH oxidase derived from *Streptococcus mutans* NCIB11723. The amino acid sequence thereof and the DNA base sequence encoding this have already been known (Patent Literature 2).

The water-forming NADH oxidase is an oxidoreductase that oxidizes the reduced coenzyme NADH to the oxidized coenzyme NAD+ and concomitantly uses molecular oxygen as an electron receptor to produce water, as described above. The reaction for producing NAD+ from NADH catalyzed by the water-forming NADH oxidase is irreversible, and produces only water as a reaction product other than NAD+.

Mutations that may be introduced into the amino acid sequence of SEQ ID No:1 are designed based on three concepts: (I) appropriate protection of the thiol group of the cysteine residue at the catalytic active site from contact with molecular oxygen; (II) removal of the steric hindrance of the NADH-binding site; and (III) contribution to stabilization of the three-dimensional structure of the enzyme in terms of free energy, and are basically embraced within the scope of the present invention as long as the introduced mutation(s) produce one or more of the effects. The following description is offered to illustrate the concepts for the design of mutations in detail.

(I) The mutation(s) for appropriately protecting the thiol group of the cysteine residue at the catalytic active site from contact with molecular oxygen mean that the mutation(s) can adequately prevent molecular oxygen from contacting Cys-44, which is thought to be the catalytic active site (active center) of water-forming NADH oxidase derived from *Streptococcus mutans*, so as to inhibit excessive oxidation of the thiol group.

Specifically, in order to inhibit excessive oxidation by molecular oxygen, the mutation(s) are designed such that a pocket of the catalytic active site to which molecular oxygen will be bound (space which allows molecular oxygen to come closer to the catalytic active site) is narrowed to reduce the rate of the elementary process of molecular oxygen entry. A three-dimensional structure model of the enzyme provides a three-dimensional understanding of the three-dimensional structure of a region around the catalytic active site, in particular, the pocket space. This understanding effectively helps to determine appropriate amino acid mutations and appropriate sites for introducing the mutations to adequately reduce the pocket space and therefore helps to design useful amino acid mutations.

(II) The mutation(s) for removing the steric hindrance of the NADH-binding site mean that the mutation(s) can cause a change of the kinetics of binding and dissociation between NADH and the enzyme which advantageously contributes to stabilization of the enzyme.

On the other hand, crystallographic structural analysis of apoenzymes to which NAD(P)H is not bound has revealed that oxidoreductases (flavoproteins) that utilize FAD and NAD(P)H have three-dimensional structures in which a pocket to which the nicotinamide coenzyme NAD(P)H will be bound (near the isoalloxazine ring of FAD) is shielded by an aromatic amino acid (Carrillo, N. & Ceccarelli, E. A., Eur. J. Biochem. 270, 1900-1915 (2003)). This mechanism of shielding the NAD(P)H-binding pocket by an aromatic ring is generally presumed to function to influence other secondary reactions (e.g. binding to other molecules) when the shield is removed (i.e. the aromatic ring is considerably shifted). However, water-forming NADH oxidase derived from *Streptococcus mutans* has not been analyzed for such a mechanism in detail yet. In addition, for its industrial purposes, the influence on other secondary reactions does not have to be taken into account.

Then, a substitution of such an aromatic amino acid residue serving as a shield is expected to result in a change of the kinetics of binding and dissociation between NADH and the enzyme, so as to advantageously contribute to stabilization of the enzyme. From a three-dimensional structure model of the enzyme, since the aromatic amino acid residue serving as a shield is presumed to be Tyr-172, mutation designed to reduce the side chain size is considered to be effective.

(III) The mutation(s) that contribute to stabilization of the three-dimensional structure of the enzyme in terms of free energy mean that the mutation(s) can be designed to achieve higher stability of the enzyme based on comparisons of free energy differences between the wild-type and variants.

Specifically, a molecular structure model (the framework of the main chain) can be used to calculate the free energy difference observed with a shift from a denatured state to the native state by molecular simulation calculation (energy minimization calculation) based on molecular mechanics. If the free energy difference is advantageous to the native state, the thermodynamic stability is also high. More specifically, free energy differences between the wild-type and various variants can be calculated by computational screening using the program Shrike (JP 2001-184381 A), and amino acid mutation candidates can then be designed based on the effect of each amino acid substitution on the free energy difference.

In the present invention, the design of "mutation(s)" can be accomplished by using a three-dimensional structure model of water-forming NADH oxidase derived from *Streptococcus mutans* which is constructed by a three-dimensional modeling method. It should be noted that the enzyme of SEQ ID No:1 has not been examined yet by structural analysis such as X-ray crystallographic structural analysis, and therefore its three-dimensional structure remains unknown.

Specifically, first, multiple amino acid sequence alignments of the enzyme and enzymes which have high amino acid sequence homology with the amino acid sequence of the former enzyme and whose three-dimensional structures are registered in the Protein Data Bank (PDB) are constructed using the program ClustalX (Thompson, J. D. et al., Nucleic Acid Res. 22, 4673-80 (1994)). The proteins having high amino acid sequence homology with the enzyme can be selected by amino acid sequence homology search among amino acid sequences of proteins registered in PDB using the program BLAST (Altschul, Stephen F. et al., Nucleic Acids Res. 25, 3389-3402 (1997)) or PSI-BLAST (Shaffer, A. A. et al., Bioinfomatics 164, 88-489 (2000)).

Next, three-dimensional structural alignment is performed on these proteins whose three-dimensional structures are known by using a three-dimensional graphics program such as Swiss-PDB Viewer (Guex, N. & Peitsch, M. C., Electrophoresis, 18, 2714-2723 (1997)) and a three-dimensional structure comparison/similar structure search server such as VAST Search (Gibrat, J. F., et al., Curr Opin Struct Biol 6, 377 (1996)). The multiple alignments obtained beforehand based on the amino acid sequences alone are modified based on the similarity between the three-dimensional structures, and then a protein presumed to have a highly similar three-dimensional structure is selected as a template protein for molecular modeling, based on the resulting sequence alignments.

Thus, the three-dimensional structure of its complex with the coenzyme (PDB code: 2NPX) is selected as a template protein for molecular modeling. This template protein is displayed on the program Swiss PDB-Viewer, and subjected to substitution of amino acid residues to correspond to the amino acid sequence (SEQ ID No:1) of the enzyme, based on the sequence alignments. The inserted and deleted sites are replaced with the most suitable similar substructures which are searched from PDB, whereby a three-dimensional structure model can be constructed.

Based on these concepts, mutations each involving at least one selected from amino acid substitutions at positions 42,- 46, 96, 172, 196, 312, and 371 of the amino acid sequence of SEQ ID No:1 were designed.

It should be noted that amino acids used for the substitutions are basically selected from 20 proteinogenic amino acids but are intended to include non-proteinogenic amino acids and non-natural amino acids, provided that these substitutions are expected to produce the same effects as those of the later-described amino acid substitutions. Mutations at the corresponding sites accomplished by insertion, deletion, and modification are also encompassed, provided that they are expected to produce the same effects as those of the later-described amino acid substitutions. For example, introducing a deletion at position 45 and an insertion at position 47 together can result in substitution of Met at position 46 with Ala and therefore is expected to produce the same effect as that of the later-described amino acid substitution at position 46.

Specifically, amino acid substitutions that may be introduced into the amino acid sequence of SEQ ID No:1 are the following mutations (1) to (7).

(1) A substitution of Leu-42 with an amino acid that appropriately protects the thiol group of the cysteine residue at the catalytic active site from contact with molecular oxygen. Specifically, it is a substitution with an amino acid having a side-chain surface area of 100 to 200 ($Å^2$), and is preferably a substitution with Val (117 $Å^2$), Ile (140 $Å^2$), Thr (102 $Å^2$), Met (160 $Å^2$), Asn (113 $Å^2$), Gln (144 A?), Asp (106 $Å^2$), or Glu (138 $Å^2$). More preferably, it is a substitution with Met because it also advantageously contributes to stabilization in terms of free energy. The numbers in parentheses refer to the side-chain surface areas of the respective amino acids.

(2) A substitution of Met-46 with an amino acid that appropriately protects the thiol group of the cysteine residue at the catalytic active site from contact with molecular oxygen. Specifically, it is a substitution with a neutral amino acid having a side-chain surface area of 100 to 150 ($Å^2$) or an acidic amino acid having a side-chain surface area of 100 to 150 ($Å^2$), and is preferably a substitution with Val (117 $Å^2$), Leu (137 $Å^2$), Ile (140 $Å^2$), Thr (102 $Å^2$), Asp (106 $Å^2$), or Glu (138 $Å^2$). More preferably, it is a substitution with Ile because it also advantageously contributes to stabilization in terms of free energy.

(3) A substitution of Asn-96 with an amino acid that contributes to stabilization of the three-dimensional structure of the enzyme in terms of free energy. Specifically, it is a substitution with a basic amino acid, and is preferably a substitution with Lys, Arg, or His. More preferably, it is a substitution with Arg or His because they provide particularly good energy values based on calculation.

(4) A substitution of Tyr-172 with an amino acid that removes the steric hindrance of the NADH-binding site. Specifically, it is a substitution with an amino acid having a smaller side-chain surface area than Tyr (187 $Å^2$), and is preferably a substitution with Gly (0 $Å^2$), Ala (67 $Å^2$), Val (117 $Å^2$), Leu (137 $Å^2$), Ile (140 $Å^2$), Ser (80 $Å^2$), Thr (102 $Å^2$), Asn (113 $Å^2$), Gln (144 $Å^2$), Asp (106 $Å^2$), Glu (138 $Å^2$), His (151 $Å^2$), Lys (167 $Å^2$), or Phe (175 $Å^2$). More preferably, it is a substitution with Ala or Ser because they also contribute to stabilization in terms of free energy.

(5) A substitution of Thr-196 with an amino acid that contributes to stabilization of the three-dimensional structure of the enzyme in terms of free energy. Specifically, it is a substitution with a basic amino acid, and is preferably a substitution with Lys, Arg, or His. More preferably, it is a substitution with His because it provides a particularly good energy value based on calculation.

(6) A substitution of Ala-312 with an amino acid that appropriately protects the thiol group of the cysteine residue at the catalytic active site from contact with molecular oxygen. Specifically, it is a substitution with an amino acid having a larger side-chain surface area than Ala (67 $Å^2$), and is preferably a substitution with Val (117 $Å^2$), Leu (137 $Å^2$), Ile (140 $Å^2$), Thr (102 $Å^2$), Asn (113 $Å^2$), Gln (144 $Å^2$), Asp (106 $Å^2$), Glu (138 $Å^2$), His (151 $Å^2$), Lys (167 $Å^2$), Arg (196 $Å^2$), Met (160 $Å^2$), Phe (175 $Å^2$), Tyr (187 $Å^2$), or Trp (217 $Å^2$). More preferably, it is a substitution with Val or Ile because they also advantageously contribute to stabilization in terms of free energy.

(7) A substitution of Phe-371 with an amino acid that contributes to stabilization of the three-dimensional structure of the enzyme in terms of free energy. Specifically, it is a substitution with an aliphatic amino acid, an acidic amino acid, or an amino acid having a hydroxyl group-bearing side chain, and is preferably a substitution with Ala, Val, Leu, Ile, Asp, Glu, Ser, Thr, or Tyr. More preferably, it is a substitution with Ala, Val, Ile, Glu, Ser, Thr, or Tyr because they provide particularly good energy values based on calculation.

Amino acids having an acidic side chain are referred to as "acidic amino acids", amino acids having a basic side chain are referred to as "basic amino acids", and the other amino acids are referred to as "neutral amino acids". Based on their isoelectric points (pI), amino acids having a pI of 4.0 or lower are referred to as "acidic amino acids", and amino acids having a pI of 7.0 or higher are referred to as "basic amino acids". The proteinogenic amino acids are categorized as follows based on their isoelectric points (Barrett G. C., "Chemistry and Biochemistry of the Amino Acids", Champman and Hall, 1985, p. 9, Table 2.2): Asp and Glu are categorized as acidic amino acids; His, Lys, and Arg are categorized as basic amino acids; and the others are categorized as neutral amino acids.

The term "aliphatic amino acid" refers to one whose side chain is a non-cyclic carbon chain. Ala, Val, Leu, and Ile among the proteinogenic amino acids are encompassed therein.

Some of the mutations in the present invention are intended to change the side chain size so as to modify the space in the structure of the protein, and therefore the side-chain surface area is used as a design parameter. The "side-chain surface area" refers to the surface area of the side chain (contactable surface area) which accurately reflects the side chain size, and the side-chain surface area of various amino acids and the particular values are available from known information, for example, in Miller, S., "J. Mol. Biol.", 1987, 196, pp. 641-656 (the particular values of the side-chain surface area are shown in Table 2, for example).

The protein of the present invention is most preferably a protein having an amino acid sequence selected from the amino acid sequences of SEQ ID Nos:2 and 4 to 19 because they provide proteins having particularly high potential in terms of stability and activity.

The mutations in the present invention can be designed by using a three-dimensional structure model of water-forming NADH oxidase derived from *Streptococcus mutans* which is constructed by a three-dimensional modeling method, as described above. Since it is thus easy to apply the present invention to amino acid sequences having sequence identity of at least 85%, preferably at least 90%, more preferably at least 95%, and still more preferably at least 98% to the amino acid sequence of SEQ ID No:1, proteins obtained by introducing mutation(s) usable in the present invention into these amino acid sequences are also included in the scope of the present invention.

The "sequence identity" herein can be determined by amino acid sequence homology analysis using the program BLAST (Altschul, Stephen F. et al., Nucleic Acids Res. 25, 3389-3402 (1997)). For BLAST analysis, software available from National Center for Biotechnology Information and the like may be used.

The term "conformationally equivalent position" herein refers to a position that can be readily and objectively identified by amino acid sequence alignment based on the three-dimensional structures of the amino acid sequence of interest and amino acid sequences whose three-dimensional structures are known (e.g. the amino acid sequence with PDB code: 2NPX used in the present invention) using a three-dimensional structure comparison/similar structure search server such as VAST Search. The VAST Search is also available from National Center for Biotechnology Information.

Enzymes having an amino acid sequence that has sequence identity of at least 85% to that of the water-forming NADH oxidase derived from *Streptococcus mutans* (SEQ ID No:1) include NADPH oxidases (or oxidases using NADH or NADPH as a substrate). This is because it is known that even a slight difference in the amino acid sequence of the coenzyme-binding site between enzymes may cause (and can be designed to cause) a difference in the coenzyme selectivity between the enzymes (Penning T. M. & Jez J. M., Chem. Rev., 101, 3027-3046 (2001)), and therefore proteins obtained by applying the present invention are included in the scope of the present invention even if they are not NADH oxidases but NADPH oxidases.

Characteristically, water-forming NAD(P)H oxidase variants obtained by the present invention have the same enzyme activity (function) as that of the wild-type but have more improved stability than the wild-type.

Proteins including an amino acid sequence of SEQ ID No:1 which further contains at least one of the above amino acid substitutions (1) to (7) according to the present invention are essentially NADH oxidase variants characteristically having improved stability compared with the wild-type NADH oxidase having the amino acid sequence of SEQ ID No:1.

The term "improved stability" means that the remaining enzyme activity (%) of a composition containing an enzyme (hereinafter, the term "enzyme" is intended to include enzyme "variants" that maintain enzyme activity) after treatment for a predetermined period of time at a constant temperature is increased compared with an enzyme for comparison subjected to the same treatment. Examples of such treatment include, but are not limited to, storage at rest at a constant temperature (incubation) and agitation with aeration. In the present invention, the remaining enzyme activity after the treatment is calculated based on the enzyme activity (NADH oxidation activity) before the treatment which is taken as 100%.

If the remaining enzyme activity of an NADH oxidase variant of the present invention is increased compared with the remaining enzyme activity of the wild-type NADH oxidase, the produced NADH oxidase variant is determined to have improved stability. Under a treatment condition which reduces the remaining enzyme activity of the wild-type NADH oxidase to 10 to 40%, the remaining enzyme activity of the NADH oxidase variant having improved stability is higher than the remaining enzyme activity of the wild-type NADH oxidase by 10% or more, preferably by 20% or more, and more preferably by 30% or more. Although not particularly limited, one Unit is defined as the enzyme activity that oxidizes 1 µmol of NADH to NAD+ for one minute (the composition and enzyme concentration of a reaction liquid are adjusted to be the same before and after the treatment), and the NADH oxidation activity is calculated based on this definition. The treatment condition is desirably, but is not limited to, agitation with aeration in a solution with such a pH near the neutral pH as a pH of 4.0 to 10.0, preferably a pH of 5.0 to 9.0, at a constant temperature in the range of 4° C. to 80° C., preferably 15° C. to 50° C., for a predetermined period of time.

A DNA encoding the protein of the present invention can be obtained by introducing site-specific mutation(s) into the wild-type NADH oxidase DNA by a recombinant DNA technique, a PCR technique, or the like, as described below.

Specifically, a recombinant DNA technique for introducing mutation(s) performed as follows. For example, if the wild-type water-forming NADH oxidase gene includes suitable restriction enzyme recognition sequences on both sides of a target site into which a mutation is to be introduced, these sequences are cleaved by the corresponding restriction enzymes to remove the region including the mutation target site, and a DNA fragment containing the mutation only at the target site, which can be prepared by chemical synthesis or the like, is inserted by cassette mutagenesis.

Alternatively, introduction of site-specific mutation(s) by PCR can be performed as follows. One of the ends Of the wild-type water-forming NADH oxidase gene is amplified using a mutation primer containing a target mutation at a mutation target site of the wild-type water-forming NADH oxidase gene and a primer for amplification containing the sequence of that one end of the gene without mutations. The other end is amplified using another mutation primer having a complementary sequence to the former mutation primer and another primer for amplification containing the sequence of that other end of the gene without mutations. These two amplified fragments are annealed and subjected to PCR with the two primers for amplification.

The vector of the present invention can be obtained by linking (inserting) the aforementioned water-forming NADH oxidase variant DNA to an appropriate vector.

The vector into which the gene is to be inserted is not particularly limited, provided that it is self-replicable in host cells. Examples of such vectors include plasmid DNAs and phage DNAs. Specific examples of vectors for *E. coli* hosts include plasmid DNAs such as pBR322, pUC18, and pBluescript II, and phage DNAs such as EMBL3, M13, and λgt11; specific examples of vectors for yeast hosts include YEp13 and YCp50; specific examples of vectors for plant host cells include pBI121 and pBI101; and specific examples of vectors for animal host cells include pcDNAI and pcDNAI/Amp.

The transformant of the present invention can be obtained by transfecting host cells with the vector. Examples of methods for transfecting bacterial cells with the recombinant DNA include a method using calcium ions and an electroporation method. Examples of methods for transfecting yeast cells with the recombinant DNA include an electroporation method, a spheroplast method, and a lithium acetate method. Examples of methods for transfecting plant cells with the recombinant DNA include an Agrobacterium infection method, a particle gun method, and a polyethylene glycol method. Examples of methods for transfecting animal cells with the recombinant DNA include an electroporation method and a calcium phosphate method.

An enzyme variant of the present invention can be produced by culturing the aforementioned transformant on a medium to express and accumulate the enzyme variant of the present invention in the cultured cells or the culture supernatant, and collecting the enzyme variant from the culture. Thus, the "culture" herein refers to a culture liquid containing cells or the cultured cells which are obtained by culturing the transformant on a medium. The transformant can be cultured on a medium in accordance with common methods for culturing host cells. Examples of media for culturing transformants of bacteria hosts such as *E. coli* include complete media and synthetic media such as LB medium and M9 medium. Then, the cells are aerobically cultured at a temperature of 20° C. to 40° C. to accumulate the enzyme variant of the present invention therein and the enzyme variant is then recovered.

The enzyme variant of the present invention can be purified by centrifuging the culture obtained by the above culturing method to recover the product (cells are disrupted by a sonicator or the like), followed by performing one or an appropriate combination of affinity chromatography, cation- or anion-exchange chromatography, gel filtration, and the like. Whether the purified product is the target enzyme can be confirmed by common methods such as SDS polyarcylamide gel electrophoresis and western blotting. Thus, the "purification" of the culture of the transformant in the present invention refers to treatment for removing contaminants other than the target enzyme without losing the enzyme activity.

The enzyme-containing product of the present invention is obtained by purifying the culture of the transformant. Examples of the enzyme-containing product include a cell-free extract obtainable by disrupting cells, an enzyme solution obtained by purification, and a freeze-dried product of the enzyme solution.

A method for producing NAD(P)+ from NAD(P)H using the NAD(P)H oxidase variant is also included in the present invention. NAD(P)H (reduced form) is basically generated as a result of, but not limited to, the reduction of NAD(P)+ which is a side reaction of the oxidation of a compound catalyzed by an oxidoreductase that recognizes an NAD(P) coenzyme. For example, a case where NAD(P)+ is reduced to NAD(P)H by a redox catalyst rather than enzymes is also included in the present invention.

The method for producing NAD(P)+ from NAD(P)H using the NAD(P)H oxidase variant according to the present invention can be used for reaction systems involving oxidoreductases (dehydrogenases) with nicotinamide adenine dinucleotide as a coenzyme. The method of the present invention enables NADH/NADPH (reduced form) produced in such a reaction system to be converted and regenerated into NAD+/NADP+ (oxidized form) by the NAD(P)H oxidase variant.

Namely, the present invention provides water-forming NADH oxidase variants that can be used in combination with oxidoreductases that use NAD(P)+ as a coenzyme. Here, the "variants that can be used in combination" means "variants intended to be used in combination". For example, the oxidoreductase that uses NAD(P)+ as a coenzyme can be used before, during, and/or after using the water-forming NAD(P)H oxidase variant. Preferably, the oxidoreductase that uses NAD(P)+ as a coenzyme and the water-forming NADH oxidase variant are simultaneously contacted with their substrates.

Oxidoreductases are enzymes classified as EC 1 and represented by EC.1.X.X.X (X is arbitrary). Oxidoreductases that utilize as a coenzyme NAD+/NADP+ (oxidized form) regenerated by the present invention are represented by EC.1.X.1.X. Thus, for example, a method for producing an alcohol derivative or a hydroxy acid derivative using an oxidoreductase represented by EC.1.1.1.X and the NAD(P)+ regeneration system in the present invention is included in the present invention.

Likewise, the production of an amino acid derivative or a primary amine derivative using an oxidoreductase variant represented by EC.1.4.1.X and the NAD(P)+ regeneration system in the present invention is also included in the present invention. The term "derivative" refers to a compound obtained by small structural modification of a certain compound. A compound obtained by substituting a hydrogen atom or a specific group of an original compound by another atom or another group is understood to be a derivative of the original compound.

Oxidoreductases that use nicotinamide adenine dinucleotide as a coenzyme can act on other various compounds such as hydrocarbon chains, nitrogen-containing compounds, and sulfur-containing compounds as substrates, and the types of these oxidoreductases are not limited in the present invention, provided that they are used in combination with the NAD(P)+ regeneration system in the present invention.

The NAD(P)H oxidase variant can also be used in a reaction (optical resolution) for producing an optically active compound with a high enantiomeric excess from an enantiomer mixture by stereoselective oxidation catalyzed by the oxidoreductase. The optically active compound with a high enantiomeric excess to be produced is not particularly limited and the NAD(P)H oxidase variant can be used for the production of any optically active compound.

Examples of the "enantiomer mixture" include compounds having an asymmetric carbon to which a hydroxyl, amino, or formyl group, which are oxidizable by dehydrogenases, is attached. Specific examples thereof include alcohol derivatives such as diol derivatives, hydroxy acid derivatives, and amino acid derivatives. More specifically, acyclic 1,2-diols, β-hydroxycarboxylic acids, 2-amino alcohols, non-natural amino acids, and the like are mentioned.

The phrase "high enantiomeric excess" means that'the ratio of a target enantiomer in a mixture with the other enantiomer is at least 70 mol %, preferably at least about 90 mol %, and more preferably at least about 95 mole %.

The reaction conditions for use of an NAD(P)H oxidase variant obtained by the present invention depend on a substrate used, an oxidoreductase used in combination, and the like. The reaction is generally performed at a temperature of about 4° C. to 80° C., preferably about 10° C. to 50° C., and at a pH of about 4.0 to 10.0, preferably about 5.0 to 9.0. In the case that the present invention is applied as an NAD(P)+ regeneration system, the NAD(P)+ concentration is, but is not limited to, about 0.00001 to 1 mol % (w/v), and preferably about 0.00001 to 0.1 mol % (w/v) of the substrate that is catalytically oxidized by the oxidoreductase used in combination.

Since the NAD(P)H oxidase variant obtained in the present invention needs oxygen to catalyze the reaction, the reaction is preferably performed in the presence of air or relatively pure oxygen. In order to accelerate dissolution of oxygen into the reaction liquid, the reaction is preferably performed under shaking or agitation. Moreover, if the readtion is performed at a pressure higher than atmospheric pressure, the solubility of oxygen in the reaction liquid may be increased, thereby improving the reaction efficiency.

The NAD(P)H oxidase variant may be used as a completely or partially purified enzyme variant. Alternatively, a culture of a microorganism capable of producing the enzyme variant or a processed product thereof may be used. The term "culture" refers to a culture liquid including cells or the cultured cells, and the term "processed product" refers to, for example, a crude extract, freeze-dried cells, acetone-dried cells, or disrupted cells thereof, or a mixture of the foregoing. Moreover, the enzyme itself or the cells themselves may be immobilized by known methods (e.g. cross-linking, physical adsorption, entrapment) before use.

For the reaction, it is not necessary to separately culture microorganisms which respectively express the NAD(P)H oxidase variant and the oxidoreductase that is used in combination if a culture of a transformant microorganism obtained by co-transfection of host cells for the expression of both enzymes or a processed product thereof is used.

Also in the case of using a microorganism that is transformed to co-express both enzymes in the same cell, NAD (P)+ in the microorganism cells can be used to perform the reaction. Therefore, there is no need for externally adding another NAD(P)+ or the amount of NAD(P)+ added can be remarkably reduced. Such a transformant can be produced by incorporating both a DNA encoding the water-forming NADH oxidase variant and a DNA encoding the oxidoreductase used in combination in the same vector, and then transfecting host cells with the vector, or by incorporating these two DNAs into two vectors of different incompatibility groups, respectively, and then co-transfecting host cells with these two vectors.

The following description is offered to illustrate the present invention in more detail by way of Examples, which are by no means intended to limit the scope of the present invention.

EXAMPLES

Example 1

Three-dimensional Structure Modeling of NADH Oxidase Derived from *Streptococcus mutans*

The program BLAST was used to search sequences highly homologous with the amino acid sequence of SEQ ID No:1. The program used for the search was blastp and the searched database was pdb (aa_db, with the proviso that the database contains all redundant sequences). Multiple amino acid sequence alignments of the amino acid sequence of SEQ ID No:1 and various highly homologous amino acid sequences found by the search were constructed using the program ClustalX. Next, three-dimensional structural alignment is performed on these proteins whose three-dimensional structures are known by using the three-dimensional graphics program Swiss-PDBViewer and the three-dimensional structure comparison/similar structure search server VAST Search, and then the multiple alignments obtained beforehand based on the amino acid sequences alone were modified based on the similarity between the three-dimensional structures. A three-dimensional structure (PDB code: 2NPX) presumed to have high similarity was selected as a template protein for molecular modeling, based on the resulting sequence alignments. The complex of this template protein with the coenzyme bound thereto was displayed on the program Swiss PDB-Viewer, and subjected to substitution of amino acid residues to correspond to the amino acid sequence (SEQ ID No:1) of the enzyme, based on the sequence alignments. The inserted and deleted sites were replaced by the most suitable similar substructures searched from PDB, whereby a three-dimensional structure model was constructed.

In the manner described above, His-11, Leu-42, Gly-43, Gly-45, Met-46, Tyr-62, and Ala-312 were identified as sites for mutations that can appropriately protect the thiol group of the cysteine residue of the catalytic active site from contact with oxygen. Since His-11 and Tyr-62 are also catalytic residues and mutations at Gly-43 and Gly-45 may largely change the main chain structure, amino acid substitutions at other sites than these were designed.

Tyr-172 was identified as a site for a mutation that can remove the steric hindrance of the NADH-binding site, and an amino acid substitution at this site was designed.

Asn-96, Thr-196, and Phe-371 were identified as sites for mutations that contribute to stabilization of the three-dimensional structure of the enzyme in terms of free energy. Free energy differences between the wild-type and various variants were calculated by computational screening using the program Shrike (JP-A 2001-184381), and amino acid mutations were then designed based on the effect of each amino acid substitution on the free energy difference.

Proteins containing these mutations, that is, water-forming NADH oxidase variants derived from *Streptococcus mutans* are shown as SEQ ID Nos:2 and 4 to 19. The amino acid sequence of SEQ ID No:2 corresponds to the L42M variant; SEQ ID No:4 corresponds to the M46I variant; SEQ ID No:5 corresponds to the N96H variant; SEQ ID No:6 corresponds to the N96R variant; SEQ ID No:7 corresponds to the Y172A variant; SEQ ID No:8 corresponds to the Y172S variant; SEQ ID No:9 corresponds to the T196H variant; SEQ ID No:10 corresponds to the A312I variant; SEQ ID No:11 corresponds to the F371A variant; SEQ ID No:12 corresponds to the F371E variant; SEQ ID No:13 corresponds to the F371V variant; SEQ ID No:14 corresponds to the F371I variant; SEQ ID No:15 corresponds to the F371S variant; SEQ ID No:16 corresponds to the F371T variant; SEQ ID No:17 corresponds to the F371Y variant; SEQ ID No:18 corresponds to the N96R/T196H/F371A variant; and SEQ ID No:19 corresponds to the M46I/N96R/T196H/F371A variant.

Example 2

Construction of Recombinant Vector Containing NADH Oxidase Gene and Preparation of Recombinant *E. coli*

In order to obtain *E. coli* that expresses the water-forming NADH oxidase derived from *Streptococcus mutans*, a recombinant vector for transformation was constructed by the method described in Patent Literature 3. *E. coli* HB101 (Takara Inc.) was transformed with the obtained recombinant vector (pNTNX). As a result, recombinant *E. coli* HB101 (pNTNX) was obtained. The DNA sequence encoding the wild-type NADH oxidase is shown as SEQ ID No:20.

Example 3

Construction of Recombinant Vectors Containing NADH Oxidase Variant Genes and Preparation of Recombinant *E. coli*

Recombinant plasmids respectively containing the NADH oxidase variant genes were obtained by quick change mutagenesis using a pair of synthetic primers designed to introduce mutation(s) at the target site(s) in the DNA sequence encoding the NADH oxidase and the recombinant plasmid pNTNX as a template. The quick change mutagenesis was performed using the QuickChange Site-Directed Mutagenesis Kit (Stratagene Corp.) in accordance with the attached protocol. By way of example, the used pairs of synthetic primers and the resulting variants are described below. For the NADH oxidase variant of SEQ ID No:2 (coding DNA sequence: SEQ ID No:21) including the mutation L42M, a recombinant vector (pNTNX-L042M) for the NADH oxidase L42M variant was obtained by quick change mutagenesis using two synthetic primers of SEQ ID Nos:22 and 23. Appropriate pairs of synthetic primers were designed and used in the same manner to prepare recombinant vectors of SEQ ID Nos:4 to 19 for the respective NADH oxidase variants. For preparation of the variants including multiple mutations of SEQ ID Nos:18 and 19, pNTNX into which a mutation had been introduced was used as a template recombinant plasmid and another mutation was introduced thereto by quick change mutagenesis. The recombinant vectors respectively containing the NADH oxidase variant genes were used to transform *E. coli* HB101 in the same manner as in Example 1, whereby various recombinant *E. coli* cells were obtained.

Example 4

Expression of NADH Oxidase in Recombinant *E. coli*

The various recombinant *E. coli* HB101 cells obtained in Examples 2 and 3 were respectively inoculated on semisynthetic media (1.5% (w/v) glycerin, 0.3% (w/v) yeast extract, 0.6% (w/v) $Na_2HPO_4$, 0.3% (w/v) $KH_2PO_4$, 0.2% (w/v) NaCl, 0.5% (w/v) $MgSO_4 \cdot 7H_2O$, 100 μg/ml ampicillin, pH 7.2), and grown at 37° C. for 38 hours. After collecting cells and removing the culture supernatant from each of the cultures, the residue was suspended in a buffer (50 mM potassium phosphate, pH 7.0) in an amount equivalent to that of the medium and ultrasonically disrupted to provide a cell-free extract. All of the enzyme variant-containing cell-free extracts were found to have NADH oxidase activity under the following measurement conditions.

[Measurement Conditions for NADH Oxidase Activity]

To 0.95 mL of a reaction liquid containing 0.17 mM NADH, 0.2 mM EDTA, and 0.02 mM FAD in a 50 mM potassium phosphate buffer (pH 7.0) was added 0.05 mL of the enzyme liquid (and optionally diluted with the buffer). The mixture was measured at a constant temperature (25° C.) for decrease in absorbance at a wavelength of 340 nm. Under these reaction conditions, one Unit was defined as the enzyme activity that oxidizes 1 μmol of NADH to NAD+ for one minute.

Example 5

Stability of Water-Forming NADH Oxidase Variant in the Presence of Oxygen

The HB101 cell-free extracts respectively containing the wild-type water-forming NADH oxidase (control) and the water-forming NADH oxidase variants prepared in Example 4 were diluted with the potassium phosphate buffer to adjust the decrease in absorbance at 340 nm for one minute to about 0.1 to 0.4, and incubated for a predetermined period of time at a constant temperature of 30° C. or 40° C. The enzyme activity was measured before and after the incubation, and the remaining enzyme activity (%) was calculated for the enzymes. The measurements were performed in several runs, and the wild-type water-forming NADH oxidase was used as a control in each run. Table 1 shows the results. The measurements were basically performed under oxygen supply, and the effect of agitation by a stirrer was also investigated in the final measurement.

TABLE 1

| Measurement | Wild | N96R | N96H | T196H | M46I |
|---|---|---|---|---|---|
| 30° C./18 hours | 37% | 49% | 51% | 53% | 61% |
| 40° C./8 hours | 14% | 25% | 23% | 27% | 53% |

| Measurement | Wild | F371S | F371V | F371A | F371I | F371Y | F371E | F371T |
|---|---|---|---|---|---|---|---|---|
| 30° C./19 hours | 33% | 44% | 40% | 48% | 51% | 42% | 43% | 50% |
| 40° C./8 hours | 17% | 34% | 32% | 42% | 43% | 35% | 32% | 43% |

| Measurement | Wild | N96R/T196H/F371A | M46I/N96R/T196H/F371A |
|---|---|---|---|
| 30° C./19 hours | 33% | 53% | 80% |

| Measurement | Wild | Y172S | Y172A |
|---|---|---|---|
| 40° C./8 hours | 13% | 34% | 24% |

| Measurement | Wild | L42M | A312I | Y172S | M46I |
|---|---|---|---|---|---|
| 25° C./6 hours, agitation (−) | 54% | 78% | 76% | 88% | 92% |
| 25° C./6 hours, agitation (+) | 29% | 60% | 73% | 44% | 56% |

The water-forming NADH oxidase variants maintained higher enzyme activity than that of the wild-type at 30° C. and also maintained high enzyme activity at 40° C. Although the remaining enzyme activity was reduced by agitation with incubation at the same temperature condition for the same period of time, the fact remains true that the variants maintained higher enzyme activity compared with the wild-type.

The invention claimed is:

1. An isolated DNA encoding a protein which has NADH oxidase activity or NADPH oxidase activity or both and has improved stability compared to the protein having the amino acid sequence of SEQ ID NO: 1, and wherein said protein has an amino acid sequence that has at least 95% sequence identity to the amino acid sequence of SEQ ID NO: 1 and further contains at least one amino acid substitution selected from (a) to (g):

(a) a substitution of an amino acid residue at a position corresponding to position 42 of SEQ ID NO: 1 with an amino acid having a side-chain surface area of 100 to 200 Å$^2$;

(b) a substitution of an amino acid residue at a position corresponding to position 46 of SEQ ID NO:1 with a neutral amino acid having a side-chain surface area of 100 to 150 Å$^2$ or an acidic amino acid having a side-chain surface area of 100 to 150 Å$^2$;

(c) a substitution of an amino acid residue at a position corresponding to position 96 of SEQ ID NO:1 with a basic amino acid;

(d) a substitution of an amino acid residue at a position corresponding to position 172 of SEQ ID NO: 1 with an amino acid having a smaller side-chain surface area than Tyr;

(e) a substitution of an amino acid residue at a position corresponding to position 196 of SEQ ID NO:1 with a basic amino acid;

(f) a substitution of an amino acid residue at a position corresponding to position 312 of SEQ ID NO: 1 with an amino acid having a larger side-chain surface area than Ala; and (g) a substitution of an amino acid residue at a position corresponding to position 371 of SEQ ID NO: 1 with an aliphatic amino acid, an acidic amino acid, or an amino acid having a hydroxyl group-bearing side chain.

2. A vector comprising the DNA according to claim 1.

3. A transformant obtained by transformation of a host cell with the vector according to claim 2.

4. A culture of the transformant according to claim 3.

5. The isolated DNA according to claim 1, wherein the amino acid sequence contains at least one amino acid substitution selected from (a) to (g):

(a) a substitution of an amino acid residue at a position corresponding to position 42 of SEQ ID NO:1 with Met;

(b) a substitution of an amino acid residue at a position corresponding to position 46 of SEQ ID NO:1 with Ile;
(c) a substitution of an amino acid residue at a position corresponding to position 96 of SEQ ID NO:1 with Arg or His;
(d) a substitution of an amino acid residue at a position corresponding to position 172 of SEQ ID NO:1 with Ala or Ser;
(e) a substitution of an amino acid residue at a position corresponding to position 196 of SEQ ID NO:1 with His;
(f) a substitution of an amino acid residue at a position corresponding to position 312 of SEQ ID NO:1 with Ile; and
(g) a substitution of an amino acid residue at a position corresponding to position 371 of SEQ ID NO:1 with Ala, Val, Ile, Glu, Ser, Thr, or Tyr.

6. An isolated DNA that encodes a protein which comprises an amino acid sequence identical to SEQ ID NO: 1 except for one or more substitutions selected from the group consisting of:
(a) a substitution of Leu at position 42 of SEQ ID NO: 1 with an amino acid having a side-chain surface area of 100 to 200 Å$^2$;
(b) a substitution of Met at position 46 of SEQ ID NO: 1 with a neutral amino acid having a side-chain surface area of 100 to 150 Å$^2$ or an acidic amino acid having a side-chain surface area of 100 to 150 Å$^2$;
(c) a substitution of Asn at position 96 of SEQ ID NO: 1 with a basic amino acid;
(d) a substitution of Tyr at position 172 of SEQ ID NO: 1 with an amino acid having a smaller side-chain surface area than Tyr;
(e) a substitution of Thr at position 196 of SEQ ID NO: 1 with a basic amino acid;
(f) a substitution of Ala at positon 312 with an amino acid having a larger side-chain surface area than Ala; and
(g) a substitution of Phe at position 371 of SEQ ID NO: 1 with an aliphatic amino acid, an acidic amino acid, or an amino acid having a hydroxyl group-bearing side chain.

7. The isolated DNA according to claim 6 wherein said protein comprises an amino acid sequence identical to SEQ ID NO: 1 except for one or more substitutions selected from the group consisting of:
(a) a substitution of Leu at position 42 of SEQ ID NO: 1 with Met;
(b) a substitution of Met at position 46 of SEQ ID NO: 1 with Ile;
(c) a substitution of Asn at position 96 of SEQ ID NO: 1 with Arg or His;
(d) a substitution of Tyr at position 172 of SEQ ID NO: 1 with Ala or Ser;
(e) a substitution of Thr at position 196 of SEQ ID NO: 1 with His;
(f) a substitution of Ala at positon 312 with Ile; and
(g) a substitution of Phe at position 371 of SEQ ID NO: 1 with Ala, Val, Ile, Glu, Ser, Thr, or Tyr.

8. An isolated DNA encoding a protein having an amino acid sequence selected from the amino acid sequences of SEQ ID Nos:2 and 4 to 19.

* * * * *

SEQUENCE LISTING

<160> NUMBER OF SEQ ID NOS: 24

<210> SEQ ID NO 1
<211> LENGTH: 457
<212> TYPE: PRT
<213> ORGANISM: Streptococcus mutans

<400> SEQUENCE: 1

```
Met Ser Lys Ile Val Ile Val Gly Ala Asn His Ala Gly Thr Ala Ala
1               5                   10                  15

Ile Asn Thr Ile Leu Asp Asn Tyr Gly Ser Glu Asn Glu Val Val Val
            20                  25                  30

Phe Asp Gln Asn Ser Asn Ile Ser Phe Leu Gly Cys Gly Met Ala Leu
        35                  40                  45

Trp Ile Gly Lys Gln Ile Ser Gly Pro Gln Gly Leu Phe Tyr Ala Asp
    50                  55                  60

Lys Glu Ser Leu Glu Ala Lys Gly Ala Lys Ile Tyr Met Glu Ser Pro
65                  70                  75                  80

Val Thr Ala Ile Asp Tyr Asp Ala Lys Arg Val Thr Ala Leu Val Asn
                85                  90                  95

Gly Gln Glu His Val Glu Ser Tyr Glu Lys Leu Ile Leu Ala Thr Gly
            100                 105                 110

Ser Thr Pro Ile Leu Pro Pro Ile Lys Gly Ala Ala Ile Lys Glu Gly
        115                 120                 125

Ser Arg Asp Phe Glu Ala Thr Leu Lys Asn Leu Gln Phe Val Lys Leu
    130                 135                 140

Tyr Gln Asn Ala Glu Asp Val Ile Asn Lys Leu Gln Asp Lys Ser Gln
145                 150                 155                 160

Asn Leu Asn Arg Ile Ala Val Val Gly Ala Gly Tyr Ile Gly Val Glu
                165                 170                 175

Leu Ala Glu Ala Phe Lys Arg Leu Gly Lys Glu Val Ile Leu Ile Asp
            180                 185                 190

Val Val Asp Thr Cys Leu Ala Gly Tyr Tyr Asp Gln Asp Leu Ser Glu
        195                 200                 205

Met Met Arg Gln Asn Leu Glu Asp His Gly Ile Glu Leu Ala Phe Gly
    210                 215                 220

Glu Thr Val Lys Ala Ile Glu Gly Asp Gly Lys Val Glu Arg Ile Val
225                 230                 235                 240

Thr Asp Lys Ala Ser His Asp Val Asp Met Val Ile Leu Ala Val Gly
                245                 250                 255

Phe Arg Pro Asn Thr Ala Leu Gly Asn Ala Lys Leu Lys Thr Phe Arg
            260                 265                 270

Asn Gly Ala Phe Leu Val Asp Lys Lys Gln Glu Thr Ser Ile Pro Asp
        275                 280                 285

Val Tyr Ala Ile Gly Asp Cys Ala Thr Val Tyr Asp Asn Ala Ile Asn
    290                 295                 300

Asp Thr Asn Tyr Ile Ala Leu Ala Ser Asn Ala Leu Arg Ser Gly Ile
305                 310                 315                 320

Val Ala Gly His Asn Ala Ala Gly His Lys Leu Glu Ser Leu Gly Val
                325                 330                 335

Gln Gly Ser Asn Gly Ile Ser Ile Phe Gly Leu Asn Met Val Ser Thr
            340                 345                 350

Gly Leu Thr Gln Glu Lys Ala Lys Arg Phe Gly Tyr Asn Pro Glu Val
        355                 360                 365

Thr Ala Phe Thr Asp Phe Gln Lys Ala Ser Phe Ile Glu His Asp Asn
    370                 375                 380

Tyr Pro Val Thr Leu Lys Ile Val Tyr Asp Lys Asp Ser Arg Leu Val
385                 390                 395                 400

Leu Gly Ala Gln Met Ala Ser Lys Glu Asp Met Ser Met Gly Ile His
                405                 410                 415
```

```
Met Phe Ser Leu Ala Ile Gln Glu Lys Val Thr Ile Glu Arg Leu Ala
            420                 425                 430

Leu Leu Asp Tyr Phe Phe Leu Pro His Phe Asn Gln Pro Tyr Asn Tyr
            435                 440                 445

Met Thr Lys Ala Ala Leu Lys Ala Lys
            450                 455

<210> SEQ ID NO 2
<211> LENGTH: 457
<212> TYPE: PRT
<213> ORGANISM: Artificial
<220> FEATURE:
<223> OTHER INFORMATION: NOX mutant

<400> SEQUENCE: 2

Met Ser Lys Ile Val Ile Val Gly Ala Asn His Ala Gly Thr Ala Ala
1               5                   10                  15

Ile Asn Thr Ile Leu Asp Asn Tyr Gly Ser Glu Asn Glu Val Val Val
            20                  25                  30

Phe Asp Gln Asn Ser Asn Ile Ser Phe Met Gly Cys Gly Met Ala Leu
            35                  40                  45

Trp Ile Gly Lys Gln Ile Ser Gly Pro Gln Gly Leu Phe Tyr Ala Asp
        50                  55                  60

Lys Glu Ser Leu Glu Ala Lys Gly Ala Lys Ile Tyr Met Glu Ser Pro
65                  70                  75                  80

Val Thr Ala Ile Asp Tyr Asp Ala Lys Arg Val Thr Ala Leu Val Asn
                85                  90                  95

Gly Gln Glu His Val Glu Ser Tyr Glu Lys Leu Ile Leu Ala Thr Gly
            100                 105                 110

Ser Thr Pro Ile Leu Pro Pro Ile Lys Gly Ala Ala Ile Lys Glu Gly
            115                 120                 125

Ser Arg Asp Phe Glu Ala Thr Leu Lys Asn Leu Gln Phe Val Lys Leu
            130                 135                 140

Tyr Gln Asn Ala Glu Asp Val Ile Asn Lys Leu Gln Asp Lys Ser Gln
145                 150                 155                 160

Asn Leu Asn Arg Ile Ala Val Gly Ala Gly Tyr Ile Gly Val Glu
            165                 170                 175

Leu Ala Glu Ala Phe Lys Arg Leu Gly Lys Glu Val Ile Leu Ile Asp
            180                 185                 190

Val Val Asp Thr Cys Leu Ala Gly Tyr Tyr Asp Gln Asp Leu Ser Glu
            195                 200                 205

Met Met Arg Gln Asn Leu Glu Asp His Gly Ile Glu Leu Ala Phe Gly
            210                 215                 220

Glu Thr Val Lys Ala Ile Glu Gly Asp Gly Lys Val Glu Arg Ile Val
225                 230                 235                 240

Thr Asp Lys Ala Ser His Asp Val Asp Met Val Ile Leu Ala Val Gly
                245                 250                 255

Phe Arg Pro Asn Thr Ala Leu Gly Asn Ala Lys Leu Lys Thr Phe Arg
            260                 265                 270

Asn Gly Ala Phe Leu Val Asp Lys Lys Gln Glu Thr Ser Ile Pro Asp
            275                 280                 285

Val Tyr Ala Ile Gly Asp Cys Ala Thr Val Tyr Asp Asn Ala Ile Asn
            290                 295                 300

Asp Thr Asn Tyr Ile Ala Leu Ala Ser Asn Ala Leu Arg Ser Gly Ile
305                 310                 315                 320
```

```
Val Ala Gly His Asn Ala Ala Gly His Lys Leu Glu Ser Leu Gly Val
            325                 330                 335

Gln Gly Ser Asn Gly Ile Ser Ile Phe Gly Leu Asn Met Val Ser Thr
            340                 345                 350

Gly Leu Thr Gln Glu Lys Ala Lys Arg Phe Gly Tyr Asn Pro Glu Val
            355                 360                 365

Thr Ala Phe Thr Asp Phe Gln Lys Ala Ser Phe Ile Glu His Asp Asn
370                 375                 380

Tyr Pro Val Thr Leu Lys Ile Val Tyr Asp Lys Asp Ser Arg Leu Val
385                 390                 395                 400

Leu Gly Ala Gln Met Ala Ser Lys Glu Asp Met Ser Met Gly Ile His
            405                 410                 415

Met Phe Ser Leu Ala Ile Gln Glu Lys Val Thr Ile Glu Arg Leu Ala
            420                 425                 430

Leu Leu Asp Tyr Phe Phe Leu Pro His Phe Asn Gln Pro Tyr Asn Tyr
            435                 440                 445

Met Thr Lys Ala Ala Leu Lys Ala Lys
            450                 455

<210> SEQ ID NO 3
<211> LENGTH: 457
<212> TYPE: PRT
<213> ORGANISM: Artificial
<220> FEATURE:
<223> OTHER INFORMATION: NOX mutant

<400> SEQUENCE: 3

Met Ser Lys Ile Val Ile Val Gly Ala Asn His Ala Gly Thr Ala Ala
1               5                   10                  15

Ile Asn Thr Ile Leu Asp Asn Tyr Gly Ser Glu Asn Glu Val Val Val
            20                  25                  30

Phe Asp Gln Asn Ser Asn Ile Ser Phe Leu Gly Cys Gly Ala Ala Leu
        35                  40                  45

Trp Ile Gly Lys Gln Ile Ser Gly Pro Gln Gly Leu Phe Tyr Ala Asp
    50                  55                  60

Lys Glu Ser Leu Glu Ala Lys Gly Ala Lys Ile Tyr Met Glu Ser Pro
65                  70                  75                  80

Val Thr Ala Ile Asp Tyr Asp Ala Lys Arg Val Thr Ala Leu Val Asn
            85                  90                  95

Gly Gln Glu His Val Glu Ser Tyr Glu Lys Leu Ile Leu Ala Thr Gly
            100                 105                 110

Ser Thr Pro Ile Leu Pro Pro Ile Lys Gly Ala Ala Ile Lys Glu Gly
        115                 120                 125

Ser Arg Asp Phe Glu Ala Thr Leu Lys Asn Leu Gln Phe Val Lys Leu
    130                 135                 140

Tyr Gln Asn Ala Glu Asp Val Ile Asn Lys Leu Gln Asp Lys Ser Gln
145                 150                 155                 160

Asn Leu Asn Arg Ile Ala Val Val Gly Ala Gly Tyr Ile Gly Val Glu
            165                 170                 175

Leu Ala Glu Ala Phe Lys Arg Leu Gly Lys Glu Val Ile Leu Ile Asp
            180                 185                 190

Val Val Asp Thr Cys Leu Ala Gly Tyr Tyr Asp Gln Asp Leu Ser Glu
        195                 200                 205

Met Met Arg Gln Asn Leu Glu Asp His Gly Ile Glu Leu Ala Phe Gly
    210                 215                 220
```

```
Glu Thr Val Lys Ala Ile Glu Gly Asp Gly Lys Val Glu Arg Ile Val
225                 230                 235                 240

Thr Asp Lys Ala Ser His Asp Val Asp Met Val Ile Leu Ala Val Gly
                245                 250                 255

Phe Arg Pro Asn Thr Ala Leu Gly Asn Ala Lys Leu Lys Thr Phe Arg
            260                 265                 270

Asn Gly Ala Phe Leu Val Asp Lys Lys Gln Glu Thr Ser Ile Pro Asp
        275                 280                 285

Val Tyr Ala Ile Gly Asp Cys Ala Thr Val Tyr Asp Asn Ala Ile Asn
    290                 295                 300

Asp Thr Asn Tyr Ile Ala Leu Ala Ser Asn Ala Leu Arg Ser Gly Ile
305                 310                 315                 320

Val Ala Gly His Asn Ala Ala Gly His Lys Leu Glu Ser Leu Gly Val
                325                 330                 335

Gln Gly Ser Asn Gly Ile Ser Ile Phe Gly Leu Asn Met Val Ser Thr
            340                 345                 350

Gly Leu Thr Gln Glu Lys Ala Lys Arg Phe Gly Tyr Asn Pro Glu Val
        355                 360                 365

Thr Ala Phe Thr Asp Phe Gln Lys Ala Ser Phe Ile Glu His Asp Asn
    370                 375                 380

Tyr Pro Val Thr Leu Lys Ile Val Tyr Asp Lys Asp Ser Arg Leu Val
385                 390                 395                 400

Leu Gly Ala Gln Met Ala Ser Lys Glu Asp Met Ser Met Gly Ile His
                405                 410                 415

Met Phe Ser Leu Ala Ile Gln Glu Lys Val Thr Ile Glu Arg Leu Ala
            420                 425                 430

Leu Leu Asp Tyr Phe Phe Leu Pro His Phe Asn Gln Pro Tyr Asn Tyr
        435                 440                 445

Met Thr Lys Ala Ala Leu Lys Ala Lys
    450                 455

<210> SEQ ID NO 4
<211> LENGTH: 457
<212> TYPE: PRT
<213> ORGANISM: Artificial
<220> FEATURE:
<223> OTHER INFORMATION: NOX mutant

<400> SEQUENCE: 4

Met Ser Lys Ile Val Ile Val Gly Ala Asn His Ala Gly Thr Ala Ala
1               5                   10                  15

Ile Asn Thr Ile Leu Asp Asn Tyr Gly Ser Glu Asn Glu Val Val Val
            20                  25                  30

Phe Asp Gln Asn Ser Asn Ile Ser Phe Leu Gly Cys Gly Ile Ala Leu
        35                  40                  45

Trp Ile Gly Lys Gln Ile Ser Gly Pro Gln Gly Leu Phe Tyr Ala Asp
    50                  55                  60

Lys Glu Ser Leu Glu Ala Lys Gly Ala Lys Ile Tyr Met Glu Ser Pro
65                  70                  75                  80

Val Thr Ala Ile Asp Tyr Asp Ala Lys Arg Val Thr Ala Leu Val Asn
                85                  90                  95

Gly Gln Glu His Val Glu Ser Tyr Gly Lys Leu Ile Leu Ala Thr Gly
            100                 105                 110

Ser Thr Pro Ile Leu Pro Pro Ile Lys Gly Ala Ala Ile Lys Glu Gly
        115                 120                 125
```

Ser Arg Asp Phe Glu Ala Thr Leu Lys Asn Leu Gln Phe Val Lys Leu
130                 135                 140

Tyr Gln Asn Ala Glu Asp Val Ile Asn Lys Leu Gln Asp Lys Ser Gln
145                 150                 155                 160

Asn Leu Asn Arg Ile Ala Val Val Gly Ala Gly Tyr Ile Gly Val Glu
            165                 170                 175

Leu Ala Glu Ala Phe Lys Arg Leu Gly Lys Glu Val Ile Leu Ile Asp
            180                 185                 190

Val Val Asp Thr Cys Leu Ala Gly Tyr Tyr Asp Gln Asp Leu Ser Glu
            195                 200                 205

Met Met Arg Gln Asn Leu Glu Asp His Gly Ile Glu Leu Ala Phe Gly
210                 215                 220

Glu Thr Val Lys Ala Ile Glu Gly Asp Gly Lys Val Glu Arg Ile Val
225                 230                 235                 240

Thr Asp Lys Ala Ser His Asp Val Asp Met Val Ile Leu Ala Val Gly
            245                 250                 255

Phe Arg Pro Asn Thr Ala Leu Gly Asn Ala Lys Leu Lys Thr Phe Arg
            260                 265                 270

Asn Gly Ala Phe Leu Val Asp Lys Lys Gln Glu Thr Ser Ile Pro Asp
            275                 280                 285

Val Tyr Ala Ile Gly Asp Cys Ala Thr Val Tyr Asp Asn Ala Ile Asn
290                 295                 300

Asp Thr Asn Tyr Ile Ala Leu Ala Ser Asn Ala Leu Arg Ser Gly Ile
305                 310                 315                 320

Val Ala Gly His Asn Ala Gly His Lys Leu Glu Ser Leu Gly Val
            325                 330                 335

Gln Gly Ser Asn Gly Ile Ser Ile Phe Gly Leu Asn Met Val Ser Thr
            340                 345                 350

Gly Leu Thr Gln Glu Lys Ala Lys Arg Phe Gly Tyr Asn Pro Glu Val
            355                 360                 365

Thr Ala Phe Thr Asp Phe Gln Lys Ala Ser Phe Ile Glu His Asp Asn
370                 375                 380

Tyr Pro Val Thr Leu Lys Ile Val Tyr Asp Lys Asp Ser Arg Leu Val
385                 390                 395                 400

Leu Gly Ala Gln Met Ala Ser Lys Glu Asp Met Ser Met Gly Ile His
            405                 410                 415

Met Phe Ser Leu Ala Ile Gln Glu Lys Val Thr Ile Glu Arg Leu Ala
            420                 425                 430

Leu Leu Asp Tyr Phe Phe Leu Pro His Phe Asn Gln Pro Tyr Asn Tyr
            435                 440                 445

Met Thr Lys Ala Ala Leu Lys Ala Lys
    450                 455

<210> SEQ ID NO 5
<211> LENGTH: 457
<212> TYPE: PRT
<213> ORGANISM: Artificial
<220> FEATURE:
<223> OTHER INFORMATION: NOX mutant

<400> SEQUENCE: 5

Met Ser Lys Ile Val Ile Val Gly Ala Asn His Ala Gly Thr Ala Ala
1               5                   10                  15

Ile Asn Thr Ile Leu Asp Asn Tyr Gly Ser Glu Asn Glu Val Val Val
            20                  25                  30

```
            Phe Asp Gln Asn Ser Asn Ile Ser Phe Leu Gly Cys Gly Met Ala Leu
                         35                  40                  45

Trp Ile Gly Lys Gln Ile Ser Gly Pro Gln Gly Leu Phe Tyr Ala Asp
             50                  55                  60

Lys Glu Ser Leu Glu Ala Lys Gly Ala Lys Ile Tyr Met Glu Ser Pro
             65                  70                  75                  80

Val Thr Ala Ile Asp Tyr Asp Ala Lys Arg Val Thr Ala Leu Val His
                             85                  90                  95

Gly Gln Glu His Val Glu Ser Tyr Glu Lys Leu Ile Leu Ala Thr Gly
                            100                 105                 110

Ser Thr Pro Ile Leu Pro Pro Ile Lys Gly Ala Ala Ile Lys Glu Gly
                        115                 120                 125

Ser Arg Asp Phe Glu Ala Thr Leu Lys Asn Leu Gln Phe Val Lys Leu
                        130                 135                 140

Tyr Gln Asn Ala Glu Asp Val Ile Asn Lys Leu Gln Asp Lys Ser Gln
            145                 150                 155                 160

Asn Leu Asn Arg Ile Ala Val Val Gly Ala Gly Tyr Ile Gly Val Glu
                            165                 170                 175

Leu Ala Glu Ala Phe Lys Arg Leu Gly Lys Glu Val Ile Leu Ile Asp
                        180                 185                 190

Val Val Asp Thr Cys Leu Ala Gly Tyr Tyr Asp Gln Asp Leu Ser Glu
                        195                 200                 205

Met Met Arg Gln Asn Leu Glu Asp His Gly Ile Glu Leu Ala Phe Gly
                        210                 215                 220

Glu Thr Val Lys Ala Ile Glu Gly Asp Gly Lys Val Glu Arg Ile Val
            225                 230                 235                 240

Thr Asp Lys Ala Ser His Asp Val Asp Met Val Ile Leu Ala Val Gly
                            245                 250                 255

Phe Arg Pro Asn Thr Ala Leu Gly Asn Ala Lys Leu Lys Thr Phe Arg
                        260                 265                 270

Asn Gly Ala Phe Leu Val Asp Lys Lys Gln Glu Thr Ser Ile Pro Asp
                        275                 280                 285

Val Tyr Ala Ile Gly Asp Cys Ala Thr Val Tyr Asp Asn Ala Ile Asn
                        290                 295                 300

Asp Thr Asn Tyr Ile Ala Leu Ala Ser Asn Ala Leu Arg Ser Gly Ile
            305                 310                 315                 320

Val Ala Gly His Asn Ala Ala Gly His Lys Leu Glu Ser Leu Gly Val
                            325                 330                 335

Gln Gly Ser Asn Gly Ile Ser Ile Phe Gly Leu Asn Met Val Ser Thr
                        340                 345                 350

Gly Leu Thr Gln Glu Lys Ala Lys Arg Phe Gly Tyr Asn Pro Glu Val
                        355                 360                 365

Thr Ala Phe Thr Asp Phe Gln Lys Ala Ser Phe Ile Glu His Asp Asn
                        370                 375                 380

Tyr Pro Val Thr Leu Lys Ile Val Tyr Asp Lys Asp Ser Arg Leu Val
            385                 390                 395                 400

Leu Gly Ala Gln Met Ala Ser Lys Glu Asp Met Ser Met Gly Ile His
                            405                 410                 415

Met Phe Ser Leu Ala Ile Gln Glu Lys Val Thr Ile Glu Arg Leu Ala
                        420                 425                 430

Leu Leu Asp Tyr Phe Phe Leu Pro His Phe Asn Gln Pro Tyr Asn Tyr
                        435                 440                 445
```

```
Met Thr Lys Ala Ala Leu Lys Ala Lys
    450                 455
```

<210> SEQ ID NO 6
<211> LENGTH: 457
<212> TYPE: PRT
<213> ORGANISM: Artificial
<220> FEATURE:
<223> OTHER INFORMATION: NOX mutant

<400> SEQUENCE: 6

```
Met Ser Lys Ile Val Ile Val Gly Ala Asn His Ala Gly Thr Ala Ala
1               5                   10                  15

Ile Asn Thr Ile Leu Asp Asn Tyr Gly Ser Glu Asn Glu Val Val Val
            20                  25                  30

Phe Asp Gln Asn Ser Asn Ile Ser Phe Leu Gly Cys Gly Met Ala Leu
        35                  40                  45

Trp Ile Gly Lys Gln Ile Ser Gly Pro Gln Gly Leu Phe Tyr Ala Asp
    50                  55                  60

Lys Glu Ser Leu Glu Ala Lys Gly Ala Lys Ile Tyr Met Glu Ser Pro
65                  70                  75                  80

Val Thr Ala Ile Asp Tyr Asp Ala Lys Arg Val Thr Ala Leu Val Arg
                85                  90                  95

Gly Gln Glu His Val Glu Ser Tyr Glu Lys Leu Ile Leu Ala Thr Gly
            100                 105                 110

Ser Thr Pro Ile Leu Pro Pro Ile Lys Gly Ala Ala Ile Lys Glu Gly
        115                 120                 125

Ser Arg Asp Phe Glu Ala Thr Leu Lys Asn Leu Gln Phe Val Lys Leu
    130                 135                 140

Tyr Gln Asn Ala Glu Asp Val Ile Asn Lys Leu Gln Asp Lys Ser Gln
145                 150                 155                 160

Asn Leu Asn Arg Ile Ala Val Val Gly Ala Gly Tyr Ile Gly Val Glu
                165                 170                 175

Leu Ala Glu Ala Phe Lys Arg Leu Gly Lys Glu Val Ile Leu Ile Asp
            180                 185                 190

Val Val Asp Thr Cys Leu Ala Gly Tyr Tyr Asp Gln Asp Leu Ser Glu
        195                 200                 205

Met Met Arg Gln Asn Leu Glu Asp His Gly Ile Glu Leu Ala Phe Gly
    210                 215                 220

Glu Thr Val Lys Ala Ile Glu Gly Asp Gly Lys Val Glu Arg Ile Val
225                 230                 235                 240

Thr Asp Lys Ala Ser His Asp Val Asp Met Val Ile Leu Ala Val Gly
                245                 250                 255

Phe Arg Pro Asn Thr Ala Leu Gly Asn Ala Lys Leu Lys Thr Phe Arg
            260                 265                 270

Asn Gly Ala Phe Leu Val Asp Lys Lys Gln Glu Thr Ser Ile Pro Asp
        275                 280                 285

Val Tyr Ala Ile Gly Asp Cys Ala Thr Val Tyr Asp Asn Ala Ile Asn
    290                 295                 300

Asp Thr Asn Tyr Ile Ala Leu Ala Ser Asn Ala Leu Arg Ser Gly Ile
305                 310                 315                 320

Val Ala Gly His Asn Ala Ala Gly His Lys Leu Glu Ser Leu Gly Val
                325                 330                 335

Gln Gly Ser Asn Gly Ile Ser Ile Phe Gly Leu Asn Met Val Ser Thr
            340                 345                 350
```

```
Gly Leu Thr Gln Glu Lys Ala Lys Arg Phe Gly Tyr Asn Pro Glu Val
            355                 360                 365

Thr Ala Phe Thr Asp Phe Gln Lys Ala Ser Phe Ile Glu His Asp Asn
    370                 375                 380

Tyr Pro Val Thr Leu Lys Ile Val Tyr Asp Lys Asp Ser Arg Leu Val
385                 390                 395                 400

Leu Gly Ala Gln Met Ala Ser Lys Glu Asp Met Ser Met Gly Ile His
                405                 410                 415

Met Phe Ser Leu Ala Ile Gln Glu Lys Val Thr Ile Glu Arg Leu Ala
            420                 425                 430

Leu Leu Asp Tyr Phe Phe Leu Pro His Phe Asn Gln Pro Tyr Asn Tyr
            435                 440                 445

Met Thr Lys Ala Ala Leu Lys Ala Lys
    450                 455

<210> SEQ ID NO 7
<211> LENGTH: 457
<212> TYPE: PRT
<213> ORGANISM: Artificial
<220> FEATURE:
<223> OTHER INFORMATION: NOX mutant

<400> SEQUENCE: 7

Met Ser Lys Ile Val Ile Val Gly Ala Asn His Ala Gly Thr Ala Ala
1               5                   10                  15

Ile Asn Thr Ile Leu Asp Asn Tyr Gly Ser Glu Asn Glu Val Val Val
                20                  25                  30

Phe Asp Gln Asn Ser Asn Ile Ser Phe Leu Gly Cys Gly Met Ala Leu
            35                  40                  45

Trp Ile Gly Lys Gln Ile Ser Gly Pro Gln Gly Leu Phe Tyr Ala Asp
    50                  55                  60

Lys Glu Ser Leu Glu Ala Lys Gly Ala Lys Ile Tyr Met Glu Ser Pro
65                  70                  75                  80

Val Thr Ala Ile Asp Tyr Asp Ala Lys Arg Val Thr Ala Leu Val Asn
                85                  90                  95

Gly Gln Glu His Val Glu Ser Tyr Glu Lys Leu Ile Leu Ala Thr Gly
            100                 105                 110

Ser Thr Pro Ile Leu Pro Pro Ile Lys Gly Ala Ala Ile Lys Glu Gly
            115                 120                 125

Ser Arg Asp Phe Glu Ala Thr Leu Lys Asn Leu Gln Phe Val Lys Leu
    130                 135                 140

Tyr Gln Asn Ala Glu Asp Val Ile Asn Lys Leu Gln Asp Lys Ser Gln
145                 150                 155                 160

Asn Leu Asn Arg Ile Ala Val Val Gly Ala Gly Ala Ile Gly Val Glu
                165                 170                 175

Leu Ala Glu Ala Phe Lys Arg Leu Gly Lys Glu Val Ile Leu Ile Asp
            180                 185                 190

Val Val Asp Thr Cys Leu Ala Gly Tyr Tyr Asp Gln Asp Leu Ser Glu
            195                 200                 205

Met Met Arg Gln Asn Leu Glu Asp His Gly Ile Glu Leu Ala Phe Gly
    210                 215                 220

Glu Thr Val Lys Ala Ile Glu Gly Asp Gly Lys Val Glu Arg Ile Val
225                 230                 235                 240

Thr Asp Lys Ala Ser His Asp Val Asp Met Val Ile Leu Ala Val Gly
                245                 250                 255
```

-continued

```
Phe Arg Pro Asn Thr Ala Leu Gly Asn Ala Lys Leu Lys Thr Phe Arg
                260                 265                 270

Asn Gly Ala Phe Leu Val Asp Lys Lys Gln Glu Thr Ser Ile Pro Asp
            275                 280                 285

Val Tyr Ala Ile Gly Asp Cys Ala Thr Val Tyr Asp Asn Ala Ile Asn
        290                 295                 300

Asp Thr Asn Tyr Ile Ala Leu Ala Ser Asn Ala Leu Arg Ser Gly Ile
305                 310                 315                 320

Val Ala Gly His Asn Ala Ala Gly His Lys Leu Glu Ser Leu Gly Val
                325                 330                 335

Gln Gly Ser Asn Gly Ile Ser Ile Phe Gly Leu Asn Met Val Ser Thr
            340                 345                 350

Gly Leu Thr Gln Glu Lys Ala Lys Arg Phe Gly Tyr Asn Pro Glu Val
        355                 360                 365

Thr Ala Phe Thr Asp Phe Gln Lys Ala Ser Phe Ile Glu His Asp Asn
370                 375                 380

Tyr Pro Val Thr Leu Lys Ile Val Tyr Asp Lys Asp Ser Arg Leu Val
385                 390                 395                 400

Leu Gly Ala Gln Met Ala Ser Lys Glu Asp Met Ser Met Gly Ile His
                405                 410                 415

Met Phe Ser Leu Ala Ile Gln Glu Lys Val Thr Ile Glu Arg Leu Ala
            420                 425                 430

Leu Leu Asp Tyr Phe Phe Leu Pro His Phe Asn Gln Pro Tyr Asn Tyr
        435                 440                 445

Met Thr Lys Ala Ala Leu Lys Ala Lys
        450                 455

<210> SEQ ID NO 8
<211> LENGTH: 457
<212> TYPE: PRT
<213> ORGANISM: Artificial
<220> FEATURE:
<223> OTHER INFORMATION: NOX mutant

<400> SEQUENCE: 8

Met Ser Lys Ile Val Ile Val Gly Ala Asn His Ala Gly Thr Ala Ala
1               5                   10                  15

Ile Asn Thr Ile Leu Asp Asn Tyr Gly Ser Glu Asn Glu Val Val Val
            20                  25                  30

Phe Asp Gln Asn Ser Asn Ile Ser Phe Leu Gly Cys Gly Met Ala Leu
        35                  40                  45

Trp Ile Gly Lys Gln Ile Ser Gly Pro Gln Gly Leu Phe Tyr Ala Asp
    50                  55                  60

Lys Glu Ser Leu Glu Ala Lys Gly Ala Lys Ile Tyr Met Glu Ser Pro
65                  70                  75                  80

Val Thr Ala Ile Asp Tyr Asp Ala Lys Arg Val Thr Ala Leu Val Asn
                85                  90                  95

Gly Gln Glu His Val Glu Ser Tyr Glu Lys Leu Ile Leu Ala Thr Gly
            100                 105                 110

Ser Thr Pro Ile Leu Pro Pro Ile Lys Gly Ala Ala Ile Lys Glu Gly
        115                 120                 125

Ser Arg Asp Phe Glu Ala Thr Leu Lys Asn Leu Gln Phe Val Lys Leu
    130                 135                 140

Tyr Gln Asn Ala Glu Asp Val Ile Asn Lys Leu Gln Asp Lys Ser Gln
145                 150                 155                 160
```

```
Asn Leu Asn Arg Ile Ala Val Val Gly Ala Gly Ser Ile Gly Val Glu
                165                 170                 175

Leu Ala Glu Ala Phe Lys Arg Leu Gly Lys Glu Val Ile Leu Ile Asp
            180                 185                 190

Val Val Asp Thr Cys Leu Ala Gly Tyr Tyr Asp Gln Asp Leu Ser Glu
        195                 200                 205

Met Met Arg Gln Asn Leu Glu Asp His Gly Ile Glu Leu Ala Phe Gly
    210                 215                 220

Glu Thr Val Lys Ala Ile Glu Gly Asp Gly Lys Val Glu Arg Ile Val
225                 230                 235                 240

Thr Asp Lys Ala Ser His Asp Val Asp Met Val Ile Leu Ala Val Gly
                245                 250                 255

Phe Arg Pro Asn Thr Ala Leu Gly Asn Ala Lys Leu Lys Thr Phe Arg
            260                 265                 270

Asn Gly Ala Phe Leu Val Asp Lys Lys Gln Glu Thr Ser Ile Pro Asp
        275                 280                 285

Val Tyr Ala Ile Gly Asp Cys Ala Thr Val Tyr Asp Asn Ala Ile Asn
    290                 295                 300

Asp Thr Asn Tyr Ile Ala Leu Ala Ser Asn Ala Leu Arg Ser Gly Ile
305                 310                 315                 320

Val Ala Gly His Asn Ala Ala Gly His Lys Leu Glu Ser Leu Gly Val
                325                 330                 335

Gln Gly Ser Asn Gly Ile Ser Ile Phe Gly Leu Asn Met Val Ser Thr
            340                 345                 350

Gly Leu Thr Gln Glu Lys Ala Lys Arg Phe Gly Tyr Asn Pro Glu Val
        355                 360                 365

Thr Ala Phe Thr Asp Phe Gln Lys Ala Ser Phe Ile Glu His Asp Asn
    370                 375                 380

Tyr Pro Val Thr Leu Lys Ile Val Tyr Asp Lys Asp Ser Arg Leu Val
385                 390                 395                 400

Leu Gly Ala Gln Met Ala Ser Lys Glu Asp Met Ser Met Gly Ile His
                405                 410                 415

Met Phe Ser Leu Ala Ile Gln Glu Lys Val Thr Ile Glu Arg Leu Ala
            420                 425                 430

Leu Leu Asp Tyr Phe Phe Leu Pro His Phe Asn Gln Pro Tyr Asn Tyr
        435                 440                 445

Met Thr Lys Ala Ala Leu Lys Ala Lys
    450                 455

<210> SEQ ID NO 9
<211> LENGTH: 457
<212> TYPE: PRT
<213> ORGANISM: Artificial
<220> FEATURE:
<223> OTHER INFORMATION: NOX mutant

<400> SEQUENCE: 9

Met Ser Lys Ile Val Ile Val Gly Ala Asn His Ala Gly Thr Ala Ala
1               5                   10                  15

Ile Asn Thr Ile Leu Asp Asn Tyr Gly Ser Glu Asn Glu Val Val Val
            20                  25                  30

Phe Asp Gln Asn Ser Asn Ile Ser Phe Leu Gly Cys Gly Met Ala Leu
        35                  40                  45

Trp Ile Gly Lys Gln Ile Ser Gly Pro Gln Gly Leu Phe Tyr Ala Asp
    50                  55                  60
```

```
Lys Glu Ser Leu Glu Ala Lys Gly Ala Lys Ile Tyr Met Glu Ser Pro
 65                  70                  75                  80

Val Thr Ala Ile Asp Tyr Asp Ala Lys Arg Val Thr Ala Leu Val Asn
                 85                  90                  95

Gly Gln Glu His Val Glu Ser Tyr Glu Lys Leu Ile Leu Ala Thr Gly
            100                 105                 110

Ser Thr Pro Ile Leu Pro Pro Ile Lys Gly Ala Ala Ile Lys Glu Gly
        115                 120                 125

Ser Arg Asp Phe Glu Ala Thr Leu Lys Asn Leu Gln Phe Val Lys Leu
    130                 135                 140

Tyr Gln Asn Ala Glu Asp Val Ile Asn Lys Leu Gln Asp Lys Ser Gln
145                 150                 155                 160

Asn Leu Asn Arg Ile Ala Val Val Gly Ala Gly Tyr Ile Gly Val Glu
                165                 170                 175

Leu Ala Glu Ala Phe Lys Arg Leu Gly Lys Glu Val Ile Leu Ile Asp
                180                 185                 190

Val Val Asp His Cys Leu Ala Gly Tyr Tyr Asp Gln Asp Leu Ser Glu
            195                 200                 205

Met Met Arg Gln Asn Leu Glu Asp His Gly Ile Glu Leu Ala Phe Gly
        210                 215                 220

Glu Thr Val Lys Ala Ile Glu Gly Asp Gly Lys Val Glu Arg Ile Val
225                 230                 235                 240

Thr Asp Lys Ala Ser His Asp Val Asp Met Val Ile Leu Ala Val Gly
                245                 250                 255

Phe Arg Pro Asn Thr Ala Leu Gly Asn Ala Lys Leu Lys Thr Phe Arg
                260                 265                 270

Asn Gly Ala Phe Leu Val Asp Lys Lys Gln Glu Thr Ser Ile Pro Asp
            275                 280                 285

Val Tyr Ala Ile Gly Asp Cys Ala Thr Val Tyr Asp Asn Ala Ile Asn
        290                 295                 300

Asp Thr Asn Tyr Ile Ala Leu Ala Ser Asn Ala Leu Arg Ser Gly Ile
305                 310                 315                 320

Val Ala Gly His Asn Ala Ala Gly His Lys Leu Glu Ser Leu Gly Val
                325                 330                 335

Gln Gly Ser Asn Gly Ile Ser Ile Phe Gly Leu Asn Met Val Ser Thr
            340                 345                 350

Gly Leu Thr Gln Glu Lys Ala Lys Arg Phe Gly Tyr Asn Pro Glu Val
        355                 360                 365

Thr Ala Phe Thr Asp Phe Gln Lys Ala Ser Phe Ile Glu His Asp Asn
    370                 375                 380

Tyr Pro Val Thr Leu Lys Ile Val Tyr Asp Lys Asp Ser Arg Leu Val
385                 390                 395                 400

Leu Gly Ala Gln Met Ala Ser Lys Glu Asp Met Ser Met Gly Ile His
                405                 410                 415

Met Phe Ser Leu Ala Ile Gln Glu Lys Val Thr Ile Glu Arg Leu Ala
            420                 425                 430

Leu Leu Asp Tyr Phe Phe Leu Pro His Phe Asn Gln Pro Tyr Asn Tyr
        435                 440                 445

Met Thr Lys Ala Ala Leu Lys Ala Lys
    450                 455

<210> SEQ ID NO 10
<211> LENGTH: 457
<212> TYPE: PRT
```

<213> ORGANISM: Artificial
<220> FEATURE:
<223> OTHER INFORMATION: NOX mutant

<400> SEQUENCE: 10

```
Met Ser Lys Ile Val Ile Val Gly Ala Asn His Ala Gly Thr Ala Ala
1               5                   10                  15

Ile Asn Thr Ile Leu Asp Asn Tyr Gly Ser Glu Asn Glu Val Val Val
            20                  25                  30

Phe Asp Gln Asn Ser Asn Ile Ser Phe Leu Gly Cys Gly Met Ala Leu
        35                  40                  45

Trp Ile Gly Lys Gln Ile Ser Gly Pro Gln Gly Leu Phe Tyr Ala Asp
    50                  55                  60

Lys Glu Ser Leu Glu Ala Lys Gly Ala Lys Ile Tyr Met Glu Ser Pro
65                  70                  75                  80

Val Thr Ala Ile Asp Tyr Asp Ala Lys Arg Val Thr Ala Leu Val Asn
                85                  90                  95

Gly Gln Glu His Val Glu Ser Tyr Glu Lys Leu Ile Leu Ala Thr Gly
            100                 105                 110

Ser Thr Pro Ile Leu Pro Pro Ile Lys Gly Ala Ala Ile Lys Glu Gly
        115                 120                 125

Ser Arg Asp Phe Glu Ala Thr Leu Lys Asn Leu Gln Phe Val Lys Leu
    130                 135                 140

Tyr Gln Asn Ala Glu Asp Val Ile Asn Lys Leu Gln Asp Lys Ser Gln
145                 150                 155                 160

Asn Leu Asn Arg Ile Ala Val Val Gly Ala Gly Tyr Ile Gly Val Glu
                165                 170                 175

Leu Ala Glu Ala Phe Lys Arg Leu Gly Lys Glu Val Ile Leu Ile Asp
            180                 185                 190

Val Val Asp Thr Cys Leu Ala Gly Tyr Tyr Asp Gln Asp Leu Ser Glu
        195                 200                 205

Met Met Arg Gln Asn Leu Glu Asp His Gly Ile Glu Leu Ala Phe Gly
    210                 215                 220

Glu Thr Val Lys Ala Ile Glu Gly Asp Gly Lys Val Glu Arg Ile Val
225                 230                 235                 240

Thr Asp Lys Ala Ser His Asp Val Asp Met Val Ile Leu Ala Val Gly
                245                 250                 255

Phe Arg Pro Asn Thr Ala Leu Gly Asn Ala Lys Leu Lys Thr Phe Arg
            260                 265                 270

Asn Gly Ala Phe Leu Val Asp Lys Lys Gln Glu Thr Ser Ile Pro Asp
        275                 280                 285

Val Tyr Ala Ile Gly Asp Cys Ala Thr Val Tyr Asp Asn Ala Ile Asn
    290                 295                 300

Asp Thr Asn Tyr Ile Ala Leu Ile Ser Asn Ala Leu Arg Ser Gly Ile
305                 310                 315                 320

Val Ala Gly His Asn Ala Ala Gly His Lys Leu Glu Ser Leu Gly Val
                325                 330                 335

Gln Gly Ser Asn Gly Ile Ser Ile Phe Gly Leu Asn Met Val Ser Thr
            340                 345                 350

Gly Leu Thr Gln Glu Lys Ala Lys Arg Phe Gly Tyr Asn Pro Glu Val
        355                 360                 365

Thr Ala Phe Thr Asp Phe Gln Lys Ala Ser Phe Ile Glu His Asp Asn
    370                 375                 380

Tyr Pro Val Thr Leu Lys Ile Val Tyr Asp Lys Asp Ser Arg Leu Val
```

```
            385                 390                 395                 400
Leu Gly Ala Gln Met Ala Ser Lys Glu Asp Met Ser Met Gly Ile His
                    405                 410                 415

Met Phe Ser Leu Ala Ile Gln Glu Lys Val Thr Ile Glu Arg Leu Ala
                    420                 425                 430

Leu Leu Asp Tyr Phe Phe Leu Pro His Phe Asn Gln Pro Tyr Asn Tyr
                    435                 440                 445

Met Thr Lys Ala Ala Leu Lys Ala Lys
                    450                 455

<210> SEQ ID NO 11
<211> LENGTH: 457
<212> TYPE: PRT
<213> ORGANISM: Artificial
<220> FEATURE:
<223> OTHER INFORMATION: NOX mutant

<400> SEQUENCE: 11

Met Ser Lys Ile Val Ile Val Gly Ala Asn His Ala Gly Thr Ala Ala
1               5                   10                  15

Ile Asn Thr Ile Leu Asp Asn Tyr Gly Ser Glu Asn Glu Val Val Val
                20                  25                  30

Phe Asp Gln Asn Ser Asn Ile Ser Phe Leu Gly Cys Gly Met Ala Leu
            35                  40                  45

Trp Ile Gly Lys Gln Ile Ser Gly Pro Gln Gly Leu Phe Tyr Ala Asp
        50                  55                  60

Lys Glu Ser Leu Glu Ala Lys Gly Ala Lys Ile Tyr Met Glu Ser Pro
65                  70                  75                  80

Val Thr Ala Ile Asp Tyr Asp Ala Lys Arg Val Thr Ala Leu Val Asn
                85                  90                  95

Gly Gln Glu His Val Glu Ser Tyr Glu Lys Leu Ile Leu Ala Thr Gly
                100                 105                 110

Ser Thr Pro Ile Leu Pro Pro Ile Lys Gly Ala Ala Ile Lys Glu Gly
            115                 120                 125

Ser Arg Asp Phe Glu Ala Thr Leu Lys Asn Leu Gln Phe Val Lys Leu
        130                 135                 140

Tyr Gln Asn Ala Glu Asp Val Ile Asn Lys Leu Gln Asp Lys Ser Gln
145                 150                 155                 160

Asn Leu Asn Arg Ile Ala Val Val Gly Ala Gly Tyr Ile Gly Val Glu
                165                 170                 175

Leu Ala Glu Ala Phe Lys Arg Leu Gly Lys Glu Val Ile Leu Ile Asp
                180                 185                 190

Val Val Asp Thr Cys Leu Ala Gly Tyr Tyr Asp Gln Asp Leu Ser Glu
                195                 200                 205

Met Met Arg Gln Asn Leu Glu Asp His Gly Ile Glu Leu Ala Phe Gly
            210                 215                 220

Glu Thr Val Lys Ala Ile Glu Gly Asp Gly Lys Val Glu Arg Ile Val
225                 230                 235                 240

Thr Asp Lys Ala Ser His Asp Val Asp Met Val Ile Leu Ala Val Gly
                245                 250                 255

Phe Arg Pro Asn Thr Ala Leu Gly Asn Ala Lys Leu Lys Thr Phe Arg
                260                 265                 270

Asn Gly Ala Phe Leu Val Asp Lys Lys Gln Glu Thr Ser Ile Pro Asp
            275                 280                 285

Val Tyr Ala Ile Gly Asp Cys Ala Thr Val Tyr Asp Asn Ala Ile Asn
```

```
               290                 295                 300
Asp Thr Asn Tyr Ile Ala Leu Ala Ser Asn Ala Leu Arg Ser Gly Ile
305                 310                 315                 320

Val Ala Gly His Asn Ala Ala Gly His Lys Leu Glu Ser Leu Gly Val
                325                 330                 335

Gln Gly Ser Asn Gly Ile Ser Ile Phe Gly Leu Asn Met Val Ser Thr
            340                 345                 350

Gly Leu Thr Gln Glu Lys Ala Lys Arg Phe Gly Tyr Asn Pro Glu Val
            355                 360                 365

Thr Ala Ala Thr Asp Phe Gln Lys Ala Ser Phe Ile Glu His Asp Asn
        370                 375                 380

Tyr Pro Val Thr Leu Lys Ile Val Tyr Asp Lys Asp Ser Arg Leu Val
385                 390                 395                 400

Leu Gly Ala Gln Met Ala Ser Lys Glu Asp Met Ser Met Gly Ile His
                405                 410                 415

Met Phe Ser Leu Ala Ile Gln Glu Lys Val Thr Ile Glu Arg Leu Ala
            420                 425                 430

Leu Leu Asp Tyr Phe Phe Leu Pro His Phe Asn Gln Pro Tyr Asn Tyr
            435                 440                 445

Met Thr Lys Ala Ala Leu Lys Ala Lys
        450                 455
```

<210> SEQ ID NO 12
<211> LENGTH: 457
<212> TYPE: PRT
<213> ORGANISM: Artificial
<220> FEATURE:
<223> OTHER INFORMATION: NOX mutant

<400> SEQUENCE: 12

```
Met Ser Lys Ile Val Ile Val Gly Ala Asn His Ala Gly Thr Ala Ala
1               5                   10                  15

Ile Asn Thr Ile Leu Asp Asn Tyr Gly Ser Glu Asn Glu Val Val Val
            20                  25                  30

Phe Asp Gln Asn Ser Asn Ile Ser Phe Leu Gly Cys Gly Met Ala Leu
        35                  40                  45

Trp Ile Gly Lys Gln Ile Ser Gly Pro Gln Gly Leu Phe Tyr Ala Asp
    50                  55                  60

Lys Glu Ser Leu Glu Ala Lys Gly Ala Lys Ile Tyr Met Glu Ser Pro
65                  70                  75                  80

Val Thr Ala Ile Asp Tyr Asp Ala Lys Arg Val Thr Ala Leu Val Asn
                85                  90                  95

Gly Gln Glu His Val Glu Ser Tyr Glu Lys Leu Ile Leu Ala Thr Gly
            100                 105                 110

Ser Thr Pro Ile Leu Pro Pro Ile Lys Gly Ala Ala Ile Lys Glu Gly
        115                 120                 125

Ser Arg Asp Phe Glu Ala Thr Leu Lys Asn Leu Gln Phe Val Lys Leu
    130                 135                 140

Tyr Gln Asn Ala Glu Asp Val Ile Asn Lys Leu Gln Asp Lys Ser Gln
145                 150                 155                 160

Asn Leu Asn Arg Ile Ala Val Val Gly Ala Gly Tyr Ile Gly Val Glu
                165                 170                 175

Leu Ala Glu Ala Phe Lys Arg Leu Gly Lys Glu Val Ile Leu Ile Asp
            180                 185                 190

Val Val Asp Thr Cys Leu Ala Gly Tyr Tyr Asp Gln Asp Leu Ser Glu
```

```
                195                 200                 205

Met Met Arg Gln Asn Leu Glu Asp His Gly Ile Glu Leu Ala Phe Gly
    210                 215                 220

Glu Thr Val Lys Ala Ile Glu Gly Asp Gly Lys Val Glu Arg Ile Val
225                 230                 235                 240

Thr Asp Lys Ala Ser His Asp Val Asp Met Val Ile Leu Ala Val Gly
                245                 250                 255

Phe Arg Pro Asn Thr Ala Leu Gly Asn Ala Lys Leu Lys Thr Phe Arg
                260                 265                 270

Asn Gly Ala Phe Leu Val Asp Lys Lys Gln Glu Thr Ser Ile Pro Asp
            275                 280                 285

Val Tyr Ala Ile Gly Asp Cys Ala Thr Val Tyr Asp Asn Ala Ile Asn
        290                 295                 300

Asp Thr Asn Tyr Ile Ala Leu Ala Ser Asn Ala Leu Arg Ser Gly Ile
305                 310                 315                 320

Val Ala Gly His Asn Ala Ala Gly His Lys Leu Glu Ser Leu Gly Val
                325                 330                 335

Gln Gly Ser Asn Gly Ile Ser Ile Phe Gly Leu Asn Met Val Ser Thr
            340                 345                 350

Gly Leu Thr Gln Glu Lys Ala Lys Arg Phe Gly Tyr Asn Pro Glu Val
        355                 360                 365

Thr Ala Glu Thr Asp Phe Gln Lys Ala Ser Phe Ile Glu His Asp Asn
    370                 375                 380

Tyr Pro Val Thr Leu Lys Ile Val Tyr Asp Lys Asp Ser Arg Leu Val
385                 390                 395                 400

Leu Gly Ala Gln Met Ala Ser Lys Glu Asp Met Ser Met Gly Ile His
                405                 410                 415

Met Phe Ser Leu Ala Ile Gln Glu Lys Val Thr Ile Glu Arg Leu Ala
            420                 425                 430

Leu Leu Asp Tyr Phe Phe Leu Pro His Phe Asn Gln Pro Tyr Asn Tyr
        435                 440                 445

Met Thr Lys Ala Ala Leu Lys Ala Lys
    450                 455

<210> SEQ ID NO 13
<211> LENGTH: 457
<212> TYPE: PRT
<213> ORGANISM: Artificial
<220> FEATURE:
<223> OTHER INFORMATION: NOX mutant

<400> SEQUENCE: 13

Met Ser Lys Ile Val Ile Val Gly Ala Asn His Ala Gly Thr Ala Ala
1               5                   10                  15

Ile Asn Thr Ile Leu Asp Asn Tyr Gly Ser Glu Asn Glu Val Val Val
            20                  25                  30

Phe Asp Gln Asn Ser Asn Ile Ser Phe Leu Gly Cys Gly Met Ala Leu
        35                  40                  45

Trp Ile Gly Lys Gln Ile Ser Gly Pro Gln Gly Leu Phe Tyr Ala Asp
    50                  55                  60

Lys Glu Ser Leu Glu Ala Lys Gly Ala Lys Ile Tyr Met Glu Ser Pro
65                  70                  75                  80

Val Thr Ala Ile Asp Tyr Asp Ala Lys Arg Val Thr Ala Leu Val Asn
                85                  90                  95

Gly Gln Glu His Val Glu Ser Tyr Glu Lys Leu Ile Leu Ala Thr Gly
```

```
            100                 105                 110
Ser Thr Pro Ile Leu Pro Pro Ile Lys Gly Ala Ala Ile Lys Glu Gly
        115                 120                 125

Ser Arg Asp Phe Glu Ala Thr Leu Lys Asn Leu Gln Phe Val Lys Leu
    130                 135                 140

Tyr Gln Asn Ala Glu Asp Val Ile Asn Lys Leu Gln Asp Lys Ser Gln
145                 150                 155                 160

Asn Leu Asn Arg Ile Ala Val Val Gly Ala Gly Tyr Ile Gly Val Glu
                165                 170                 175

Leu Ala Glu Ala Phe Lys Arg Leu Gly Lys Glu Val Ile Leu Ile Asp
            180                 185                 190

Val Val Asp Thr Cys Leu Ala Gly Tyr Tyr Asp Gln Asp Leu Ser Glu
        195                 200                 205

Met Met Arg Gln Asn Leu Glu Asp His Gly Ile Glu Leu Ala Phe Gly
    210                 215                 220

Glu Thr Val Lys Ala Ile Glu Gly Asp Gly Lys Val Glu Arg Ile Val
225                 230                 235                 240

Thr Asp Lys Ala Ser His Asp Val Asp Met Val Ile Leu Ala Val Gly
                245                 250                 255

Phe Arg Pro Asn Thr Ala Leu Gly Asn Ala Lys Leu Lys Thr Phe Arg
            260                 265                 270

Asn Gly Ala Phe Leu Val Asp Lys Lys Gln Glu Thr Ser Ile Pro Asp
        275                 280                 285

Val Tyr Ala Ile Gly Asp Cys Ala Thr Val Tyr Asp Asn Ala Ile Asn
    290                 295                 300

Asp Thr Asn Tyr Ile Ala Leu Ala Ser Asn Ala Leu Arg Ser Gly Ile
305                 310                 315                 320

Val Ala Gly His Asn Ala Gly His Lys Leu Glu Ser Leu Gly Val
                325                 330                 335

Gln Gly Ser Asn Gly Ile Ser Ile Phe Gly Leu Asn Met Val Ser Thr
            340                 345                 350

Gly Leu Thr Gln Glu Lys Ala Lys Arg Phe Gly Tyr Asn Pro Glu Val
        355                 360                 365

Thr Ala Val Thr Asp Phe Gln Lys Ala Ser Phe Ile Glu His Asp Asn
    370                 375                 380

Tyr Pro Val Thr Leu Lys Ile Val Tyr Asp Lys Asp Ser Arg Leu Val
385                 390                 395                 400

Leu Gly Ala Gln Met Ala Ser Lys Glu Asp Met Ser Met Gly Ile His
                405                 410                 415

Met Phe Ser Leu Ala Ile Gln Glu Lys Val Thr Ile Glu Arg Leu Ala
            420                 425                 430

Leu Leu Asp Tyr Phe Phe Leu Pro His Phe Asn Gln Pro Tyr Asn Tyr
        435                 440                 445

Met Thr Lys Ala Ala Leu Lys Ala Lys
    450                 455

<210> SEQ ID NO 14
<211> LENGTH: 457
<212> TYPE: PRT
<213> ORGANISM: Artificial
<220> FEATURE:
<223> OTHER INFORMATION: NOX mutant

<400> SEQUENCE: 14

Met Ser Lys Ile Val Ile Val Gly Ala Asn His Ala Gly Thr Ala Ala
```

-continued

```
1               5                   10                  15
Ile Asn Thr Ile Leu Asp Asn Tyr Gly Ser Glu Asn Glu Val Val Val
            20                  25                  30

Phe Asp Gln Asn Ser Asn Ile Ser Phe Leu Gly Cys Gly Met Ala Leu
            35                  40                  45

Trp Ile Gly Lys Gln Ile Ser Gly Pro Gln Gly Leu Phe Tyr Ala Asp
        50                  55                  60

Lys Glu Ser Leu Glu Ala Lys Gly Ala Lys Ile Tyr Met Glu Ser Pro
65                  70                  75                  80

Val Thr Ala Ile Asp Tyr Asp Ala Lys Arg Val Thr Ala Leu Val Asn
                85                  90                  95

Gly Gln Glu His Val Glu Ser Tyr Glu Lys Leu Ile Leu Ala Thr Gly
            100                 105                 110

Ser Thr Pro Ile Leu Pro Pro Ile Lys Gly Ala Ala Ile Lys Glu Gly
            115                 120                 125

Ser Arg Asp Phe Glu Ala Thr Leu Lys Asn Leu Gln Phe Val Lys Leu
130                 135                 140

Tyr Gln Asn Ala Glu Asp Val Ile Asn Lys Leu Gln Asp Lys Ser Gln
145                 150                 155                 160

Asn Leu Asn Arg Ile Ala Val Val Gly Ala Gly Tyr Ile Gly Val Glu
                165                 170                 175

Leu Ala Glu Ala Phe Lys Arg Leu Gly Lys Glu Val Ile Leu Ile Asp
            180                 185                 190

Val Val Asp Thr Cys Leu Ala Gly Tyr Tyr Asp Gln Asp Leu Ser Glu
            195                 200                 205

Met Met Arg Gln Asn Leu Glu Asp His Gly Ile Glu Leu Ala Phe Gly
210                 215                 220

Glu Thr Val Lys Ala Ile Glu Gly Asp Gly Lys Val Glu Arg Ile Val
225                 230                 235                 240

Thr Asp Lys Ala Ser His Asp Val Asp Met Val Ile Leu Ala Val Gly
                245                 250                 255

Phe Arg Pro Asn Thr Ala Leu Gly Asn Ala Lys Leu Lys Thr Phe Arg
            260                 265                 270

Asn Gly Ala Phe Leu Val Asp Lys Lys Gln Glu Thr Ser Ile Pro Asp
            275                 280                 285

Val Tyr Ala Ile Gly Asp Cys Ala Thr Val Tyr Asp Asn Ala Ile Asn
            290                 295                 300

Asp Thr Asn Tyr Ile Ala Leu Ala Ser Asn Ala Leu Arg Ser Gly Ile
305                 310                 315                 320

Val Ala Gly His Asn Ala Ala Gly His Lys Leu Glu Ser Leu Gly Val
                325                 330                 335

Gln Gly Ser Asn Gly Ile Ser Ile Phe Gly Leu Asn Met Val Ser Thr
            340                 345                 350

Gly Leu Thr Gln Glu Lys Ala Lys Arg Phe Gly Tyr Asn Pro Glu Val
            355                 360                 365

Thr Ala Ile Thr Asp Phe Gln Lys Ala Ser Phe Ile Glu His Asp Asn
370                 375                 380

Tyr Pro Val Thr Leu Lys Ile Val Tyr Asp Lys Asp Ser Arg Leu Val
385                 390                 395                 400

Leu Gly Ala Gln Met Ala Ser Lys Glu Asp Met Ser Met Gly Ile His
                405                 410                 415

Met Phe Ser Leu Ala Ile Gln Glu Lys Val Thr Ile Glu Arg Leu Ala
            420                 425                 430
```

```
Leu Leu Asp Tyr Phe Phe Leu Pro His Phe Asn Gln Pro Tyr Asn Tyr
        435                 440                 445

Met Thr Lys Ala Ala Leu Lys Ala Lys
    450                 455

<210> SEQ ID NO 15
<211> LENGTH: 457
<212> TYPE: PRT
<213> ORGANISM: Artificial
<220> FEATURE:
<223> OTHER INFORMATION: NOX mutant

<400> SEQUENCE: 15

Met Ser Lys Ile Val Ile Val Gly Ala Asn His Ala Gly Thr Ala Ala
1               5                   10                  15

Ile Asn Thr Ile Leu Asp Asn Tyr Gly Ser Glu Asn Glu Val Val Val
            20                  25                  30

Phe Asp Gln Asn Ser Asn Ile Ser Phe Leu Gly Cys Gly Met Ala Leu
        35                  40                  45

Trp Ile Gly Lys Gln Ile Ser Gly Pro Gln Gly Leu Phe Tyr Ala Asp
    50                  55                  60

Lys Glu Ser Leu Glu Ala Lys Gly Ala Lys Ile Tyr Met Glu Ser Pro
65                  70                  75                  80

Val Thr Ala Ile Asp Tyr Asp Ala Lys Arg Val Thr Ala Leu Val Asn
                85                  90                  95

Gly Gln Glu His Val Glu Ser Tyr Glu Lys Leu Ile Leu Ala Thr Gly
            100                 105                 110

Ser Thr Pro Ile Leu Pro Pro Ile Lys Gly Ala Ala Ile Lys Glu Gly
        115                 120                 125

Ser Arg Asp Phe Glu Ala Thr Leu Lys Asn Leu Gln Phe Val Lys Leu
    130                 135                 140

Tyr Gln Asn Ala Glu Asp Val Ile Asn Lys Leu Gln Asp Lys Ser Gln
145                 150                 155                 160

Asn Leu Asn Arg Ile Ala Val Val Gly Ala Gly Tyr Ile Gly Val Glu
                165                 170                 175

Leu Ala Glu Ala Phe Lys Arg Leu Gly Lys Glu Val Ile Leu Ile Asp
            180                 185                 190

Val Val Asp Thr Cys Leu Ala Gly Tyr Tyr Asp Gln Asp Leu Ser Glu
        195                 200                 205

Met Met Arg Gln Asn Leu Glu Asp His Gly Ile Glu Leu Ala Phe Gly
    210                 215                 220

Glu Thr Val Lys Ala Ile Glu Gly Asp Gly Lys Val Glu Arg Ile Val
225                 230                 235                 240

Thr Asp Lys Ala Ser His Asp Val Asp Met Val Ile Leu Ala Val Gly
                245                 250                 255

Phe Arg Pro Asn Thr Ala Leu Gly Asn Ala Lys Leu Lys Thr Phe Arg
            260                 265                 270

Asn Gly Ala Phe Leu Val Asp Lys Lys Gln Glu Thr Ser Ile Pro Asp
        275                 280                 285

Val Tyr Ala Ile Gly Asp Cys Ala Thr Val Tyr Asp Asn Ala Ile Asn
    290                 295                 300

Asp Thr Asn Tyr Ile Ala Leu Ala Ser Asn Ala Leu Arg Ser Gly Ile
305                 310                 315                 320

Val Ala Gly His Asn Ala Ala Gly His Lys Leu Glu Ser Leu Gly Val
                325                 330                 335
```

```
Gln Gly Ser Asn Gly Ile Ser Ile Phe Gly Leu Asn Met Val Ser Thr
            340                 345                 350

Gly Leu Thr Gln Glu Lys Ala Lys Arg Phe Gly Tyr Asn Pro Glu Val
            355                 360                 365

Thr Ala Ser Thr Asp Phe Gln Lys Ala Ser Phe Ile Glu His Asp Asn
370                 375                 380

Tyr Pro Val Thr Leu Lys Ile Val Tyr Asp Lys Asp Ser Arg Leu Val
385                 390                 395                 400

Leu Gly Ala Gln Met Ala Ser Lys Glu Asp Met Ser Met Gly Ile His
                405                 410                 415

Met Phe Ser Leu Ala Ile Gln Glu Lys Val Thr Ile Glu Arg Leu Ala
                420                 425                 430

Leu Leu Asp Tyr Phe Phe Leu Pro His Phe Asn Gln Pro Tyr Asn Tyr
            435                 440                 445

Met Thr Lys Ala Ala Leu Lys Ala Lys
        450                 455

<210> SEQ ID NO 16
<211> LENGTH: 457
<212> TYPE: PRT
<213> ORGANISM: Artificial
<220> FEATURE:
<223> OTHER INFORMATION: NOX mutant

<400> SEQUENCE: 16

Met Ser Lys Ile Val Ile Val Gly Ala Asn His Ala Gly Thr Ala Ala
1               5                   10                  15

Ile Asn Thr Ile Leu Asp Asn Tyr Gly Ser Glu Asn Glu Val Val Val
            20                  25                  30

Phe Asp Gln Asn Ser Asn Ile Ser Phe Leu Gly Cys Gly Met Ala Leu
        35                  40                  45

Trp Ile Gly Lys Gln Ile Ser Gly Pro Gln Gly Leu Phe Tyr Ala Asp
    50                  55                  60

Lys Glu Ser Leu Glu Ala Lys Gly Ala Lys Ile Tyr Met Glu Ser Pro
65                  70                  75                  80

Val Thr Ala Ile Asp Tyr Asp Ala Lys Arg Val Thr Ala Leu Val Asn
                85                  90                  95

Gly Gln Glu His Val Glu Ser Tyr Glu Lys Leu Ile Leu Ala Thr Gly
            100                 105                 110

Ser Thr Pro Ile Leu Pro Pro Ile Lys Gly Ala Ala Ile Lys Glu Gly
        115                 120                 125

Ser Arg Asp Phe Glu Ala Thr Leu Lys Asn Leu Gln Phe Val Lys Leu
    130                 135                 140

Tyr Gln Asn Ala Glu Asp Val Ile Asn Lys Leu Gln Asp Lys Ser Gln
145                 150                 155                 160

Asn Leu Asn Arg Ile Ala Val Val Gly Ala Gly Tyr Ile Gly Val Glu
                165                 170                 175

Leu Ala Glu Ala Phe Lys Arg Leu Gly Lys Glu Val Ile Leu Ile Asp
            180                 185                 190

Val Val Asp Thr Cys Leu Ala Gly Tyr Tyr Asp Gln Asp Leu Ser Glu
        195                 200                 205

Met Met Arg Gln Asn Leu Glu Asp His Gly Ile Glu Leu Ala Phe Gly
    210                 215                 220

Glu Thr Val Lys Ala Ile Glu Gly Asp Gly Lys Val Glu Arg Ile Val
225                 230                 235                 240
```

```
Thr Asp Lys Ala Ser His Asp Val Asp Met Val Ile Leu Ala Val Gly
                245                 250                 255

Phe Arg Pro Asn Thr Ala Leu Gly Asn Ala Lys Leu Lys Thr Phe Arg
            260                 265                 270

Asn Gly Ala Phe Leu Val Asp Lys Lys Gln Glu Thr Ser Ile Pro Asp
        275                 280                 285

Val Tyr Ala Ile Gly Asp Cys Ala Thr Val Tyr Asp Asn Ala Ile Asn
    290                 295                 300

Asp Thr Asn Tyr Ile Ala Leu Ala Ser Asn Ala Leu Arg Ser Gly Ile
305                 310                 315                 320

Val Ala Gly His Asn Ala Ala Gly His Lys Leu Glu Ser Leu Gly Val
                325                 330                 335

Gln Gly Ser Asn Gly Ile Ser Ile Phe Gly Leu Asn Met Val Ser Thr
            340                 345                 350

Gly Leu Thr Gln Glu Lys Ala Lys Arg Phe Gly Tyr Asn Pro Glu Val
        355                 360                 365

Thr Ala Thr Thr Asp Phe Gln Lys Ala Ser Phe Ile Glu His Asp Asn
    370                 375                 380

Tyr Pro Val Thr Leu Lys Ile Val Tyr Asp Lys Asp Ser Arg Leu Val
385                 390                 395                 400

Leu Gly Ala Gln Met Ala Ser Lys Glu Asp Met Ser Met Gly Ile His
                405                 410                 415

Met Phe Ser Leu Ala Ile Gln Glu Lys Val Thr Ile Glu Arg Leu Ala
            420                 425                 430

Leu Leu Asp Tyr Phe Phe Leu Pro His Phe Asn Gln Pro Tyr Asn Tyr
        435                 440                 445

Met Thr Lys Ala Ala Leu Lys Ala Lys
    450                 455

<210> SEQ ID NO 17
<211> LENGTH: 457
<212> TYPE: PRT
<213> ORGANISM: Artificial
<220> FEATURE:
<223> OTHER INFORMATION: NOX mutant

<400> SEQUENCE: 17

Met Ser Lys Ile Val Ile Val Gly Ala Asn His Ala Gly Thr Ala Ala
1               5                   10                  15

Ile Asn Thr Ile Leu Asp Asn Tyr Gly Ser Glu Asn Glu Val Val Val
            20                  25                  30

Phe Asp Gln Asn Ser Asn Ile Ser Phe Leu Gly Cys Gly Met Ala Leu
        35                  40                  45

Trp Ile Gly Lys Gln Ile Ser Gly Pro Gln Gly Leu Phe Tyr Ala Asp
    50                  55                  60

Lys Glu Ser Leu Glu Ala Lys Gly Ala Lys Ile Tyr Met Glu Ser Pro
65                  70                  75                  80

Val Thr Ala Ile Asp Tyr Asp Ala Lys Arg Val Thr Ala Leu Val Asn
                85                  90                  95

Gly Gln Glu His Val Glu Ser Tyr Glu Lys Leu Ile Leu Ala Thr Gly
            100                 105                 110

Ser Thr Pro Ile Leu Pro Pro Ile Lys Gly Ala Ala Ile Lys Glu Gly
        115                 120                 125

Ser Arg Asp Phe Glu Ala Thr Leu Lys Asn Leu Gln Phe Val Lys Leu
    130                 135                 140
```

Tyr Gln Asn Ala Glu Asp Val Ile Asn Lys Leu Gln Asp Lys Ser Gln
145                 150                 155                 160

Asn Leu Asn Arg Ile Ala Val Gly Ala Gly Tyr Ile Gly Val Glu
            165                 170                 175

Leu Ala Glu Ala Phe Lys Arg Leu Gly Lys Glu Val Ile Leu Ile Asp
        180                 185                 190

Val Val Asp Thr Cys Leu Ala Gly Tyr Tyr Asp Gln Asp Leu Ser Glu
            195                 200                 205

Met Met Arg Gln Asn Leu Glu Asp His Gly Ile Glu Leu Ala Phe Gly
        210                 215                 220

Glu Thr Val Lys Ala Ile Glu Gly Asp Gly Lys Val Glu Arg Ile Val
225                 230                 235                 240

Thr Asp Lys Ala Ser His Asp Val Asp Met Val Ile Leu Ala Val Gly
            245                 250                 255

Phe Arg Pro Asn Thr Ala Leu Gly Asn Ala Lys Leu Lys Thr Phe Arg
            260                 265                 270

Asn Gly Ala Phe Leu Val Asp Lys Gln Glu Thr Ser Ile Pro Asp
            275                 280                 285

Val Tyr Ala Ile Gly Asp Cys Ala Thr Val Tyr Asp Asn Ala Ile Asn
        290                 295                 300

Asp Thr Asn Tyr Ile Ala Leu Ala Ser Asn Ala Leu Arg Ser Gly Ile
305                 310                 315                 320

Val Ala Gly His Asn Ala Ala Gly His Lys Leu Glu Ser Leu Gly Val
            325                 330                 335

Gln Gly Ser Asn Gly Ile Ser Ile Phe Gly Leu Asn Met Val Ser Thr
            340                 345                 350

Gly Leu Thr Gln Glu Lys Ala Lys Arg Phe Gly Tyr Asn Pro Glu Val
            355                 360                 365

Thr Ala Tyr Thr Asp Phe Gln Lys Ala Ser Phe Ile Glu His Asp Asn
        370                 375                 380

Tyr Pro Val Thr Leu Lys Ile Val Tyr Asp Lys Asp Ser Arg Leu Val
385                 390                 395                 400

Leu Gly Ala Gln Met Ala Ser Lys Glu Asp Met Ser Met Gly Ile His
            405                 410                 415

Met Phe Ser Leu Ala Ile Gln Glu Lys Val Thr Ile Glu Arg Leu Ala
        420                 425                 430

Leu Leu Asp Tyr Phe Phe Leu Pro His Phe Asn Gln Pro Tyr Asn Tyr
            435                 440                 445

Met Thr Lys Ala Ala Leu Lys Ala Lys
        450                 455

<210> SEQ ID NO 18
<211> LENGTH: 457
<212> TYPE: PRT
<213> ORGANISM: Artificial
<220> FEATURE:
<223> OTHER INFORMATION: NOX mutant

<400> SEQUENCE: 18

Met Ser Lys Ile Val Ile Val Gly Ala Asn His Ala Gly Thr Ala Ala
1               5                   10                  15

Ile Asn Thr Ile Leu Asp Asn Tyr Gly Ser Glu Asn Glu Val Val Val
            20                  25                  30

Phe Asp Gln Asn Ser Asn Ile Ser Phe Leu Gly Cys Gly Met Ala Leu
        35                  40                  45

```
Trp Ile Gly Lys Gln Ile Ser Gly Pro Gln Gly Leu Phe Tyr Ala Asp
 50                  55                  60
Lys Glu Ser Leu Glu Ala Lys Gly Ala Lys Ile Tyr Met Glu Ser Pro
 65                  70                  75                  80
Val Thr Ala Ile Asp Tyr Asp Ala Lys Arg Val Thr Ala Leu Val Arg
                 85                  90                  95
Gly Gln Glu His Val Glu Ser Tyr Glu Lys Leu Ile Leu Ala Thr Gly
                100                 105                 110
Ser Thr Pro Ile Leu Pro Pro Ile Lys Gly Ala Ala Ile Lys Glu Gly
            115                 120                 125
Ser Arg Asp Phe Glu Ala Thr Leu Lys Asn Leu Gln Phe Val Lys Leu
            130                 135                 140
Tyr Gln Asn Ala Glu Asp Val Ile Asn Lys Leu Gln Asp Lys Ser Gln
145                 150                 155                 160
Asn Leu Asn Arg Ile Ala Val Val Gly Ala Gly Tyr Ile Gly Val Glu
                165                 170                 175
Leu Ala Glu Ala Phe Lys Arg Leu Gly Lys Glu Val Ile Leu Ile Asp
                180                 185                 190
Val Val Asp His Cys Leu Ala Gly Tyr Tyr Asp Gln Asp Leu Ser Glu
            195                 200                 205
Met Met Arg Gln Asn Leu Glu Asp His Gly Ile Glu Leu Ala Phe Gly
            210                 215                 220
Glu Thr Val Lys Ala Ile Glu Gly Asp Gly Lys Val Glu Arg Ile Val
225                 230                 235                 240
Thr Asp Lys Ala Ser His Asp Val Asp Met Val Ile Leu Ala Val Gly
                245                 250                 255
Phe Arg Pro Asn Thr Ala Leu Gly Asn Ala Lys Leu Lys Thr Phe Arg
                260                 265                 270
Asn Gly Ala Phe Leu Val Asp Lys Lys Gln Glu Thr Ser Ile Pro Asp
            275                 280                 285
Val Tyr Ala Ile Gly Asp Cys Ala Thr Val Tyr Asp Asn Ala Ile Asn
            290                 295                 300
Asp Thr Asn Tyr Ile Ala Leu Ala Ser Asn Ala Leu Arg Ser Gly Ile
305                 310                 315                 320
Val Ala Gly His Asn Ala Ala Gly His Lys Leu Glu Ser Leu Gly Val
                325                 330                 335
Gln Gly Ser Asn Gly Ile Ser Ile Phe Gly Leu Asn Met Val Ser Thr
            340                 345                 350
Gly Leu Thr Gln Glu Lys Ala Lys Arg Phe Gly Tyr Asn Pro Glu Val
            355                 360                 365
Thr Ala Ala Thr Asp Phe Gln Lys Ala Ser Phe Ile Glu His Asp Asn
            370                 375                 380
Tyr Pro Val Thr Leu Lys Ile Val Tyr Asp Lys Asp Ser Arg Leu Val
385                 390                 395                 400
Leu Gly Ala Gln Met Ala Ser Lys Glu Asp Met Ser Met Gly Ile His
                405                 410                 415
Met Phe Ser Leu Ala Ile Gln Glu Lys Val Thr Ile Glu Arg Leu Ala
                420                 425                 430
Leu Leu Asp Tyr Phe Phe Leu Pro His Phe Asn Gln Pro Tyr Asn Tyr
            435                 440                 445
Met Thr Lys Ala Ala Leu Lys Ala Lys
            450                 455
```

```
<210> SEQ ID NO 19
<211> LENGTH: 457
<212> TYPE: PRT
<213> ORGANISM: Artificial
<220> FEATURE:
<223> OTHER INFORMATION: NOX mutant

<400> SEQUENCE: 19

Met Ser Lys Ile Val Ile Val Gly Ala Asn His Ala Gly Thr Ala Ala
1               5                   10                  15

Ile Asn Thr Ile Leu Asp Asn Tyr Gly Ser Glu Asn Glu Val Val Val
                20                  25                  30

Phe Asp Gln Asn Ser Asn Ile Ser Phe Leu Gly Cys Gly Ile Ala Leu
            35                  40                  45

Trp Ile Gly Lys Gln Ile Ser Gly Pro Gln Gly Leu Phe Tyr Ala Asp
    50                  55                  60

Lys Glu Ser Leu Glu Ala Lys Gly Ala Lys Ile Tyr Met Glu Ser Pro
65                  70                  75                  80

Val Thr Ala Ile Asp Tyr Asp Ala Lys Arg Val Thr Ala Leu Val Arg
                85                  90                  95

Gly Gln Glu His Val Glu Ser Tyr Glu Lys Leu Ile Leu Ala Thr Gly
            100                 105                 110

Ser Thr Pro Ile Leu Pro Pro Ile Lys Gly Ala Ala Ile Lys Glu Gly
        115                 120                 125

Ser Arg Asp Phe Glu Ala Thr Leu Lys Asn Leu Gln Phe Val Lys Leu
130                 135                 140

Tyr Gln Asn Ala Glu Asp Val Ile Asn Lys Leu Gln Asp Lys Ser Gln
145                 150                 155                 160

Asn Leu Asn Arg Ile Ala Val Val Gly Ala Gly Tyr Ile Gly Val Glu
                165                 170                 175

Leu Ala Glu Ala Phe Lys Arg Leu Gly Lys Glu Val Ile Leu Ile Asp
            180                 185                 190

Val Val Asp His Cys Leu Ala Gly Tyr Tyr Asp Gln Asp Leu Ser Glu
        195                 200                 205

Met Met Arg Gln Asn Leu Glu Asp His Gly Ile Glu Leu Ala Phe Gly
210                 215                 220

Glu Thr Val Lys Ala Ile Glu Gly Asp Gly Lys Val Glu Arg Ile Val
225                 230                 235                 240

Thr Asp Lys Ala Ser His Asp Val Asp Met Val Ile Leu Ala Val Gly
                245                 250                 255

Phe Arg Pro Asn Thr Ala Leu Gly Asn Ala Lys Leu Lys Thr Phe Arg
            260                 265                 270

Asn Gly Ala Phe Leu Val Asp Lys Lys Gln Glu Thr Ser Ile Pro Asp
        275                 280                 285

Val Tyr Ala Ile Gly Asp Cys Ala Thr Val Tyr Asp Asn Ala Ile Asn
290                 295                 300

Asp Thr Asn Tyr Ile Ala Leu Ala Ser Asn Ala Leu Arg Ser Gly Ile
305                 310                 315                 320

Val Ala Gly His Asn Ala Ala Gly His Lys Leu Glu Ser Leu Gly Val
                325                 330                 335

Gln Gly Ser Asn Gly Ile Ser Ile Phe Gly Leu Asn Met Val Ser Thr
            340                 345                 350

Gly Leu Thr Gln Glu Lys Ala Lys Arg Phe Gly Tyr Asn Pro Glu Val
        355                 360                 365
```

Thr Ala Ala Thr Asp Phe Gln Lys Ala Ser Phe Ile Glu His Asp Asn
    370                 375                 380

Tyr Pro Val Thr Leu Lys Ile Val Tyr Asp Lys Asp Ser Arg Leu Val
385                 390                 395                 400

Leu Gly Ala Gln Met Ala Ser Lys Glu Asp Met Ser Met Gly Ile His
                405                 410                 415

Met Phe Ser Leu Ala Ile Gln Glu Lys Val Thr Ile Glu Arg Leu Ala
                420                 425                 430

Leu Leu Asp Tyr Phe Phe Leu Pro His Phe Asn Gln Pro Tyr Asn Tyr
                435                 440                 445

Met Thr Lys Ala Ala Leu Lys Ala Lys
    450                 455

<210> SEQ ID NO 20
<211> LENGTH: 1374
<212> TYPE: DNA
<213> ORGANISM: Streptococcus mutans

<400> SEQUENCE: 20
atgagtaaaa tcgttattgt tggagctaac catgcaggta cagctgccat taatactatt      60
ctagataatt acgtagtga aaacgaagtt gtcgttttg accaaaattc taatatttca       120
ttcttgggtt gtggaatggc actttggatt ggaaaacaaa tatcaggccc tcaaggtctt      180
ttttatgctg acaaggaatc gttagaagca aaaggtgcta aaatttatat ggaatcgcca      240
gtgacagcca ttgattatga tgctaagagg gttactgctt tggtcaatgg tcaagaacat     300
gttgaaagct atgagaagct tattttggca acaggatcaa caccaatctt accacctatc     360
aaaggtgcag ctatcaaaga aggtagtcgt gattttgaag caactttgaa aaatcttcaa     420
tttgttaaat tgtatcaaaa tgcagaagat gttattaata aattcacagg taagagtcaa    480
aatctgaatc gtattgctgt tgttggtgct ggttatattg gtgtagaact tgctgaagcc     540
tttaaacgcc tcggaaaaga agtgattctt attgatgttg ttgatacttg cttagctggt    600
tattatgatc aggatctttc agaaatgatg cgtcaaaatt tggaagatca tggtattgaa    660
ttagcattcg gagaaactgt caaagccatt gaaggtgatg gtaaagtcga acgtattgta    720
actgataaag cgagccatga tgtggatatg gttatttag ctgtcggttt ccgtcctaat    780
actgcacttg gcaacgctaa actcaaaacc ttccgtaatg gtgctttcct tgttgataaa    840
aaacaagaga caagtattcc tgacgtttat gccatcggcg attgcgcgac tgtttatgac    900
aacgctatta tgataccaa ttatattgcc ttagcttcaa acgctcttcg ctcaggtatt    960
gtagctggtc ataatgcagc agggcataaa ttggaatctc ttggtgttca aggttcaaat   1020
ggtatttcaa tttttggtct caatatggtt tcaactgggt taacacaaga aaaagcaaag    1080
cgttttggct ataatccaga agtcactgca tttacagatt tcagaaggc tagttttatt    1140 gaacatgata attatcctgt tacacttaaa attgtctatg ataaggatag ccgactggtt    1200
cttggtgcac aaatggcatc taagaagat atgtcaatgg gaattcacat gttttcattg    1260
gctattcagg aaaaagttac cattgaacgt ttagctctac tggactattt ctttcttcct   1320
catttcaatc aaccctataa ttatatgacc aaagcagcat taaaagctaa atga         1374

<210> SEQ ID NO 21
<211> LENGTH: 1374
<212> TYPE: DNA
<213> ORGANISM: Artificial
<220> FEATURE:
<223> OTHER INFORMATION: NOX mutant

<400> SEQUENCE: 21

```
atgagtaaaa tcgttattgt tggagctaac catgcaggta cagctgccat taatactatt    60
ctagataatt acggtagtga aaacgaagtt gtcgttttg accaaaattc taatatttca    120
ttcatgggtt gtggaatggc actttggatt ggaaaacaaa tatcaggccc tcaaggtctt    180
ttttatgctg acaaggaatc gttagaagca aaaggtgcta aaatttatat ggaatcgcca    240
gtgacagcca ttgattatga tgctaagagg gttactgctt tggtcaatgg tcaagaacat    300
gttgaaagct atgagaagct tattttggca acaggatcaa caccaatctt accacctatc    360
aaaggtgcag ctatcaaaga aggtagtcgt gattttgaag caactttgaa aaatcttcaa    420
tttgttaaat tgtatcaaaa tgcagaagat gttattaata aattacagga taagagtcaa    480
aatctgaatc gtattgctgt tgttggtgct ggttatattg gtgtagaact tgctgaagcc    540
tttaaacgcc tcggaaaaga agtgattctt attgatgttg ttgatacttg cttagctggt    600
tattatgatc aggatctttc agaaatgatg cgtcaaaatt tggaagatca tggtattgaa    660
ttagcattcg gagaaactgt caaagccatt gaaggtgatg gtaaagtcga acgtattgta    720
actgataaag cgagccatga tgtggatatg gttattttag ctgtcggttt ccgtcctaat    780
actgcacttg gcaacgctaa actcaaaacc ttccgtaatg gtgctttcct tgttgataaa    840
aaacaagaga caagtattcc tgacgtttat gccatcggcg attgcgcgac tgtttatgac    900
aacgctatta tgataccaa ttatattgcc ttagcttcaa acgctcttcg ctcaggtatt    960
gtagctggtc ataatgcagc agggcataaa ttggaatctc ttggtgttca aggttcaaat    1020
ggtatttcaa tttttggtct caatatggtt tcaactgggt taacacaaga aaaagcaaag    1080
cgttttggct ataatccaga agtcactgca tttacagatt ttcagaaggc tagttttatt    1140
gaacatgata attatcctgt tacacttaaa attgtctatg ataaggatag ccgactggtt    1200
cttggtgcac aaatggcatc taagaagat atgtcaatgg gaattcacat gttttcattg    1260
gctattcagg aaaagttac cattgaacgt ttagctctac tggactattt ctttcttcct    1320
catttcaatc aaccctataa ttatatgacc aaagcagcat taaaagctaa atga          1374
```

<210> SEQ ID NO 22
<211> LENGTH: 29
<212> TYPE: DNA
<213> ORGANISM: Artificial
<220> FEATURE:
<223> OTHER INFORMATION: synthetic DNA primer

<400> SEQUENCE: 22

```
ctaatatttc attcatgggt tgtggaatg                                        29
```

<210> SEQ ID NO 23
<211> LENGTH: 29
<212> TYPE: DNA
<213> ORGANISM: Artificial
<220> FEATURE:
<223> OTHER INFORMATION: Synthetic DNA primer

<400> SEQUENCE: 23

```
cattccacaa cccatgaatg aaatattag                                        29
```

<210> SEQ ID NO 24
<211> LENGTH: 1374
<212> TYPE: DNA
<213> ORGANISM: Artificial
<220> FEATURE:

<223> OTHER INFORMATION: NOX mutant

<400> SEQUENCE: 24

```
atgagtaaaa tcgttattgt tggagctaac catgcaggta cagctgccat taatactatt      60
ctagataatt acggtagtga aaacgaagtt gtcgtttttg accaaaattc taatatttca     120
ttcttgggtt gtggaatcgc actttggatt ggaaaacaaa tatcaggccc tcaaggtctt     180
ttttatgctg acaaggaatc gttagaagca aaaggtgcta aaatttatat ggaatcgcca     240
gtgacagcca ttgattatga tgctaagagg gttactgctt tggtcaatgg tcaagaacat     300
gttgaaagct atgagaagct tattttggca acaggatcaa caccaatctt accacctatc     360
aaaggtgcag ctatcaaaga aggtagtcgt gattttgaag caactttgaa aaatcttcaa     420
tttgttaaat tgtatcaaaa tgcagaagat gttattaata aattacagga taagagtcaa     480
aatctgaatc gtattgctgt tgttggtgct ggttatattg gtgtagaact tgctgaagcc     540
tttaaacgcc tcggaaaaga agtgattctt attgatgttg ttgatacttg cttagctggt     600
tattatgatc aggatctttc agaaatgatg cgtcaaaatt tggaagatca tggtattgaa     660
ttagcattcg gagaaactgt caaagccatt gaaggtgatg gtaaagtcga acgtattgta     720
actgataaag cgagccatga tgtggatatg gttattttag ctgtcggttt ccgtcctaat     780
actgcacttg gcaacgctaa actcaaaacc ttccgtaatg gtgctttcct tgttgataaa     840
aaacaagaga caagtattcc tgacgtttat gccatcggcg attgcgcgac tgtttatgac     900
aacgctatta atgataccaa ttatattgcc ttagcttcaa acgctcttcg ctcaggtatt     960
gtagctggtc ataatgcagc agggcataaa ttggaatctc ttggtgttca aggttcaaat    1020
ggtatttcaa tttttggtct caatatggtt tcaactgggt taacacaaga aaaagcaaag    1080
cgttttggct ataatccaga agtcactgca tttacagatt ttcagaaggc tagttttatt    1140
gaacatgata attatcctgt tacacttaaa attgtctatg ataaggatag ccgactggtt    1200
cttggtgcac aaatggcatc taagaagat atgtcaatgg gaattcacat gtttttcattg    1260
gctattcagg aaaaagttac cattgaacgt ttagctctac tggactattt ctttcttcct    1320
catttcaatc aaccctataa ttatatgacc aaagcagcat taaaagctaa atga          1374
```